United States Patent
Seko et al.

(10) Patent No.: US 9,321,819 B2
(45) Date of Patent: Apr. 26, 2016

(54) OXIDATIVE STRESS RESPONSIVE APOPTOSIS INDUCING PROTEIN EIF5A

(71) Applicant: Yoshinori Seko, Bunkyo-ku (JP)

(72) Inventors: Yoshinori Seko, Bunkyo-ku (JP);
Tsutomu Fujimura, Bunkyo-ku (JP);
Kimie Murayama, Bunkyo-ku (JP)

(73) Assignee: Yoshinori Seko, Bunkyo-ku (JP)

( * ) Notice: Subject to any disclaimer, the term of this patent is extended or adjusted under 35 U.S.C. 154(b) by 63 days.

(21) Appl. No.: 13/904,662

(22) Filed: May 29, 2013

(65) Prior Publication Data

US 2013/0280268 A1    Oct. 24, 2013

Related U.S. Application Data

(62) Division of application No. 12/994,824, filed as application No. PCT/JP2009/002344 on May 27, 2009, now Pat. No. 8,492,521.

(30) Foreign Application Priority Data

May 27, 2008 (JP) .................... 2008-137824

(51) Int. Cl.
| | |
|---|---|
| A61K 39/395 | (2006.01) |
| C07K 14/47 | (2006.01) |
| G01N 33/68 | (2006.01) |
| C07K 16/22 | (2006.01) |
| A61K 38/00 | (2006.01) |

(52) U.S. Cl.
CPC ......... *C07K 14/4747* (2013.01); *C07K 14/4702* (2013.01); *C07K 16/22* (2013.01); *G01N 33/6893* (2013.01); *A61K 38/00* (2013.01); *G01N 2800/7009* (2013.01)

(58) Field of Classification Search
None
See application file for complete search history.

(56) References Cited

U.S. PATENT DOCUMENTS

| | | | |
|---|---|---|---|
| 7,217,517 B2 * | 5/2007 | Thompson | ......... C07K 14/4747 |
| 2006/0094677 A1 | 5/2006 | Thompson | |
| 2009/0253777 A1 * | 10/2009 | Hanauske-Abel et al. | |
| 2011/0039911 A1 * | 2/2011 | Pe'ery et al. | |

FOREIGN PATENT DOCUMENTS

| | | |
|---|---|---|
| EP | 1236738 | 9/2002 |
| JP | 2005-519583 A | 7/2005 |
| JP | 2005-524410 A | 8/2005 |
| JP | 2006-507816 | 3/2006 |
| JP | 2006-520611 A | 9/2006 |
| JP | 2006-526989 A | 11/2006 |
| WO | WO 03/010286 A2 | 2/2003 |
| WO | WO 03/095613 A2 | 11/2003 |

(Continued)

OTHER PUBLICATIONS

Cracchiolo et al., Eukaryotic initiation factor 5A-1 (eIF5A-1) as a diagnostic marker for aberrant proliferation in intraepitheliial neoplasia of the vulva, Gynecol. Oncolo. 94:217-222, 2004.*

(Continued)

*Primary Examiner* — Claire Kaufman
(74) *Attorney, Agent, or Firm* — Oblon, McClelland, Maier & Neustadt, L.L.P.

(57) ABSTRACT

Secreted eIF5A protein which is useful for diagnosis, prevention, and treatment of various diseases induced by an oxidative stress.

2 Claims, 23 Drawing Sheets

(56) References Cited

FOREIGN PATENT DOCUMENTS

| WO | WO 2004/037984 A2 | 5/2004 |
|---|---|---|
| WO | WO 2004/078940 A2 | 9/2004 |
| WO | WO 2005/007853 A2 | 1/2005 |
| WO | 2009144933 | 12/2009 |

OTHER PUBLICATIONS

Kornstantakopoulos et al, Changes in gene expression elicited by physiological concetrations of genistein on human endometrial cancer cells, Mol. Carcino. 45:752-763, 2006.*
Santa Cruz Biotechnology, eIF5A antibody (C-20:sc-18939 [online]. Retrieved from the internet: <URL: http://www.scbt.com/datasheet-18939-eif5a-c-20-antibody.html>. 2007 [retrieved on Mar. 10, 2015].*
Taylor et al., eIF5A in TNF-alpha-mediated apoptosis in lamina cribrosa cells, Invest. Ophthal. Sci. 45(10):3568-3576, Oct. 2004.*
Hecquet et al., Role of TRPM2 channel in mediating H2O2-induced Ca2+ entry and endothelial hyperpermeability, Circ. Res. 102:347-355, Feb. 2008.*
Leiris et al., Oxidative stress and ischemia, Heart Metab. 31:5-7, 2006.*
BD Transduction Laboratories, Purified mouse anti-eIF-5a, Retrieved from the internet: <URL: http://www.bdbiosciences.com/ds/pm/tds/611977.pdf>, revision 2, 2011 [retrieved on Mar. 10, 2015].*
Drewe et al., Clinically useful monoclonal antibodies in treatment, J. Clin. Pathol. 55:81-85, 2002.*
Bi-Xing et al., Intracellular delivery of monoclonal antibodies, Immunol. Lett. 84:63-67, 2002.*
International Search Report issued Jun. 30, 2009 in PCT/JP2009/002344.
Catherine A. Taylor, et al., "Eukaryotic translation initiation factor 5A induces apoptosis in colon cancer cells and associates with the nucleus in response to tumour necrosis factor a signalling", Experimental Cell Research, vol. 313, No. 3, 2007, pp. 437-449.
Ai-Ling Li, et al., "A Novel eIF5A Complex Functions As a Regulator of p53 and p53-dependent Apoptosis", The Journal of Biological Chemistry, vol. 279, No. 47, Nov. 19, 2004, pp. 49251-49258.
Catherine A. Taylor, et al., "Role of eIF5A in TNF-α-Mediated Apoptosis of Lamina Cribrosa Cells", Investigative Ophthalmology & Visual Science, vol. 45, No. 10, Oct. 2004, pp. 3568-3576.
Yoshinori Seko, "Kekkan ni Okeru sanka Stress hanno o Baikai suru Seiri Kassei Busshitsu no Tanri Dotei Oyobi Kekkan Shogai no Shinten Yokusei Ryoho no Kaihatsu", Research Report of Takeda Medical Research Foundation, No. 30, 2003, pp. 16-21 (with an additional page).
Yoshinori Seko, MD, et al., "Role of Fas/FasL Pathway in the Activation of Infiltrating Cells in Murine Acute Myocarditis Caused by Coxsackievirus B3", Journal of the American College of Cardiology, vol. 39, No. 8, 2002, pp. 1399-1403.
Roberta A. Gottlieb, et al., "Reperfusion Injury Induces Apoptosis in Rabbit Cardiomyocytes", The Journal of Clinical Investigation, Inc., vol. 94, Oct. 1994, pp. 1621-1628.
Alicja E. Beilawska, et al., "Ceramide Is Involved in Triggering of Cardiomyocyte Apoptosis Induced by Ischemia and Reperfusion", American Journal of Pathology, vol. 151, No. 5, Nov. 1997, pp. 1257-1263.
M. Caraglia, et al., "The role of eukaryotic initiation factor 5A in the control of cell proliferation and apoptosis", Amino Acids, vol. 20, 2001, pp. 91-104.
Kang, et al., Tranlation initiation factor eIF-5A, the hypusin-containing protein, is phosphorylated on serine in *Saccharomyces cerevisiae*, J. Biol. Chem. 268(20):14750-14756, Jul. 15, 1993.
Mersich et al., Peptides derived from the secretory yeast library restor factor VIII activity in the presence of an inhibitory antibody, Biotech. Bioeng. 98:12-21, 2007.

* cited by examiner

SEQUENCE LISTING

```
<160> NUMBER OF SEQ ID NOS: 4

<210> SEQ ID NO 1
<211> LENGTH: 465
<212> TYPE: DNA
<213> ORGANISM: Homo sapiens
<220> FEATURE:
<221> NAME/KEY: CDS
<222> LOCATION: (1)..(462)

<400> SEQUENCE: 1 atg gca gat gac ttg gac ttc gag aca gga gat gca ggg gcc tca gcc      48
Met Ala Asp Asp Leu Asp Phe Glu Thr Gly Asp Ala Gly Ala Ser Ala
1               5                   10                  15 acc ttc cca atg cag tgc tca gca tta cgt aag aat ggc ttt gtg gtg      96
Thr Phe Pro Met Gln Cys Ser Ala Leu Arg Lys Asn Gly Phe Val Val
                20                  25                  30 ctc aaa ggc cgg cca tgt aag atc gtc gag atg tct act tcg aag act     144
Leu Lys Gly Arg Pro Cys Lys Ile Val Glu Met Ser Thr Ser Lys Thr
            35                  40                  45 ggc aag cac ggc cac gcc aag gtc cat ctg gtt ggt att gac atc ttt     192
Gly Lys His Gly His Ala Lys Val His Leu Val Gly Ile Asp Ile Phe
        50                  55                  60 act ggg aag aaa tat gaa gat atc tgc ccg tca act cat aat atg gat     240
Thr Gly Lys Lys Tyr Glu Asp Ile Cys Pro Ser Thr His Asn Met Asp
65                  70                  75                  80 gtc ccc aac atc aaa agg aat gac ttc cag ctg att ggc atc cag gat     288
Val Pro Asn Ile Lys Arg Asn Asp Phe Gln Leu Ile Gly Ile Gln Asp
                85                  90                  95 ggg tac cta tca ctg ctc cag gac agc ggg gag gta cga gag gac ctt     336
Gly Tyr Leu Ser Leu Leu Gln Asp Ser Gly Glu Val Arg Glu Asp Leu
                100                 105                 110 cgt ctc cct gag gga gac ctt ggc aag gag att gag cag aag tac gac     384
Arg Leu Pro Glu Gly Asp Leu Gly Lys Glu Ile Glu Gln Lys Tyr Asp
            115                 120                 125 tgt gga gaa gag atc ctg atc acg gtg ctg tct gcc atg aca gag gag     432
Cys Gly Glu Glu Ile Leu Ile Thr Val Leu Ser Ala Met Thr Glu Glu
        130                 135                 140 gca gct gtt gca atc aag gcc atg gca aaa taa                         465
Ala Ala Val Ala Ile Lys Ala Met Ala Lys
145                 150

<210> SEQ ID NO 2
<211> LENGTH: 26
<212> TYPE: DNA
<213> ORGANISM: Artificial sequence
<220> FEATURE:
<223> OTHER INFORMATION: Description of Artificial Sequence: Synthetic
      primer

<400> SEQUENCE: 2
```

```
caccgaattc aaaatggcag atgact                                               26

<210> SEQ ID NO 3
<211> LENGTH: 76
<212> TYPE: DNA
<213> ORGANISM: Artificial sequence
<220> FEATURE:
<223> OTHER INFORMATION: Description of Artificial Sequence: Synthetic
      primer

<400> SEQUENCE: 3
atatactcga gtcagtgatg gtgatggtgg tgcttgtcat cgtcgtcctt gtaatctttt          60
gccatggcct tgattg                                                          76

<210> SEQ ID NO 4
<211> LENGTH: 154
<212> TYPE: PRT
<213> ORGANISM: Homo sapiens

<400> SEQUENCE: 4

Met Ala Asp Asp Leu Asp Phe Glu Thr Gly Asp Ala Gly Ala Ser Ala
1               5                   10                  15

Thr Phe Pro Met Gln Cys Ser Ala Leu Arg Lys Asn Gly Phe Val Val
                20                  25                  30

Leu Lys Gly Arg Pro Cys Lys Ile Val Glu Met Ser Thr Ser Lys Thr
            35                  40                  45

Gly Lys His Gly His Ala Lys Val His Leu Val Gly Ile Asp Ile Phe
        50                  55                  60

Thr Gly Lys Lys Tyr Glu Asp Ile Cys Pro Ser Thr His Asn Met Asp
65                  70                  75                  80

Val Pro Asn Ile Lys Arg Asn Asp Phe Gln Leu Ile Gly Ile Gln Asp
                85                  90                  95

Gly Tyr Leu Ser Leu Leu Gln Asp Ser Gly Glu Val Arg Glu Asp Leu
            100                 105                 110

Arg Leu Pro Glu Gly Asp Leu Gly Lys Glu Ile Glu Gln Lys Tyr Asp
        115                 120                 125

Cys Gly Glu Glu Ile Leu Ile Thr Val Leu Ser Ala Met Thr Glu Glu
    130                 135                 140

Ala Ala Val Ala Ile Lys Ala Met Ala Lys
145                 150
```

OXIDATIVE STRESS RESPONSIVE APOPTOSIS INDUCING PROTEIN EIF5A

CROSS-REFERENCE TO RELATED APPLICATIONS

The present application is a divisional application of U.S. application Ser. No. 12/994,824 filed Feb. 23, 2011, which is incorporated herein by reference, now U.S. Pat. No. 8,492,521, which was a National Stage application of PCT/JP2009/02344, filed on May 27, 2009, and claims the benefit of Japanese patent application JP 2008-137824, filed on May 27, 2008.

TECHNICAL FIELD

The present invention relates to a protein which inhibits apoptosis, in particular, apoptosis caused by oxidative stress, and a diagnostic agent and a pharmaceutical which contain the same.

BACKGROUND ART

It is known that mammalian cells quickly respond and adapt to environmental stimuli (for example, mechanical load, metabolic changes, ischemia and reperfusion) by expressing a number of genes. Especially, oxidative stress induced by various external stresses (for example, ischemia followed by reperfusion, ultraviolet burn, and irradiation) is known to play a key role in pathogenesis of cell injury involved, which accelerates inflammation, atherosclerosis, aging, and the like.

In particular, cardiac myocytes express various genes coding for growth factors, cytokines, cell-adhesion molecules, and so on, in response to ischemia/reperfusion to adapt to these stresses, or lead to further cell damage known as reperfusion injury. The threshold of cardiac myocytes to undergo apoptosis seems to be so high to protect these non-division cells from external stresses. For example, only small part of cardiac myocytes can undergo apoptosis even in such a situation of acute myocarditis in which strong expression of Fas on cardiac myocytes and FasL on infiltrating lymphocytes was induced (Non Patent Literature 1). However, there is the only exception of the case, which is reperfusion injury. Reperfusion of ischemic tissue causes massive production of oxygen free radicals, excessive intracellular calcium influx, and neutrophil infiltration, resulting in acute inflammation associated with extensive apoptosis of cells. Because reperfusion-induced apoptotic cell death was not induced by ischemia alone, and could not be prevented by neutrophil depletion (Non Patent Literature 2), it has been proposed that some mechanism triggered by reperfusion mediates the apoptosis signaling pathway, which may precede and be independent of neutrophil infiltration (Non Patent Literature 3).

Eukaryotic translation initiation factor (eIF) 5A is a substance which was identified as a translation initiation factor as its name suggests. It is known that eIF5A is expressed in the cytoplasm, deoxyhypusinated by deoxyhypusine synthase (DHS) (deoxyhypusinated eIF5A), and after that hypusinated by deoxyhypusine hydroxylase (DOHH) (hypusinated eIF5A), and that this hypusinated eIF5A exhibits a cell proliferative action (Non Patent Literature 4). However, it has not been known at all that eIF5A is secreted extracellularly, and what role the secreted eIF5A plays in induction of apoptosis.

CITATION LIST

Non Patent Literature

[Non Patent Literature 1] J. Am. Coll. Cardiol. 39, 1399-1403 (2002)

[Non Patent Literature 2] J. Clin. Invest. 94, 1621-1628 (1994)

[Non Patent Literature 3] Am. J. Pathol. 151, 1257-1263 (1997)

[Non Patent Literature 4] Amino Acids 20, 91-104 (2001)

SUMMARY OF INVENTION

Problem to be Solved by the Invention

An object of the present invention is to provide an agent which is useful for diagnosis, prevention, and treatment of various diseases induced by oxidative stress.

Solution to Problem

Accordingly, the inventors of the present invention adopted cultured cells which were subjected to hypoxia/reoxygenation as an in vitro model of ischemia followed by reperfusion, in which cell injury, that is, apoptosis is known to be caused by oxidative stress. The inventors of the present invention considered that a certain humoral factor released from cultured cells exposed to the hypoxia/reoxygenation condition is involved in apoptosis and analyzed the humoral factor. As a result, the inventors of the present invention found that eIF5A, which has been heretofore reported to be present only in the cytoplasm, is secreted extracellularly from cells exposed to the hypoxia/reoxygenation condition, that is, under an oxidative stress condition, and that the secreted eIF5A is a novel protein as it clearly differs from the eIF5A present in the cytoplasm with regards to the isoelectric point.

Furthermore, the inventors of the present invention found that when a cell is exposed to hypoxia/reoxygenation, that is, an oxidative stress, the secreted eIF5A is secreted extracellularly, acts as an apoptosis-inducing ligand, and induces apoptosis of the cells exposed to oxidative stress, and hence oxidative stress can be diagnosed by measuring the secreted eIF5A.

Furthermore, the inventors of the present invention found that the apoptosis can be significantly inhibited by allowing an anti-eIF5A neutralizing antibody to act as a representative substance which inhibits secreted eIF5A. The present invention was thus accomplished.

Specifically, the present invention provides a secreted eIF5A protein.

The present invention further provides a pharmaceutical containing a secreted eIF5A protein.

The present invention further provides a method for determining an oxidative stress, including measuring a secreted eIF5A protein in a fluid or a tissue specimen The present invention further provides a diagnostic agent for oxidative stress, containing a reagent for measuring a secreted eIF5A protein.

The present invention further provides an apoptosis inhibitor, containing a secreted eIF5A protein inhibitor.

The present invention further provides use of a secreted eIF5A protein for production of an apoptosis inducer.

The present invention further provides use of a secreted eIF5A protein inhibitor for production of an apoptosis inhibitor.

The present invention further provides a method for inducing apoptosis, including administering a secreted eIF5A protein.

The present invention further provides a method for inhibiting apoptosis, including administering a secreted eIF5A protein inhibitor.

Advantageous Effects of Invention

As a secreted eIF5A protein of the present invention is an entirely new protein which is secreted from a mammalian cell when the cell is exposed to an oxidative stress, an oxidative stress condition of mammals including humans can be determined and diagnosed by measuring the secreted eIF5A protein. Specifically, whether or not cell injury caused by an oxidative stress may occur or cell injury has already occurred can be diagnosed.

Furthermore, as the secreted eIF5A protein induces not only apoptosis caused by an oxidative stress, but apoptosis at a normoxic concentration, the secreted eIF5A protein is useful as a therapeutic agent for cancer and diseases represented by infiltrative diseases.

Furthermore, as a secreted eIF5A protein inhibitor inhibits apoptosis caused by an oxidative stress, the secreted eIF5A protein inhibitor is useful as a preventive or therapeutic pharmaceutical for not only ischemia/reperfusion injury and ultraviolet ray/radiation damage, but also atherosclerosis, aging, and the like accelerated by an oxidative stress.

BRIEF DESCRIPTION OF DRAWINGS

FIG. 3g shows electron microscopic determination of hypercondensation of nuclear chromatin induced by recombinant eIF5A (RCP).

FIG. 3h shows the effects of a PARP-1 inhibitor (3-aminobenzamide, 2 mM) or caspase inhibitor (Z-VAD.fmk, 100 μM), added at 1 hour before addition of recombinant eIF5A (RCP), on the induction of apoptosis of cardiac myocytes by double immunostaining for TUNEL (brown color) and cardiac myosin (blue color) (P<0.001*: n=4).

FIG. 3j shows the effect of immunodepletion of eIF5A on reoxygenation-conditioned media (RCM)-induced apoptosis of cardiac myocytes by double immunostaining for TUNEL (brown color) and cardiac myosin (blue color) at 30 hours after adding RCM.

FIG. 6 is a diagram showing the apoptosis inducing ability (TUNEL staining) of recombinant eIF5A (re-eIF5A) on various cells.

MODES FOR CARRYING OUT THE INVENTION

Figure 1:
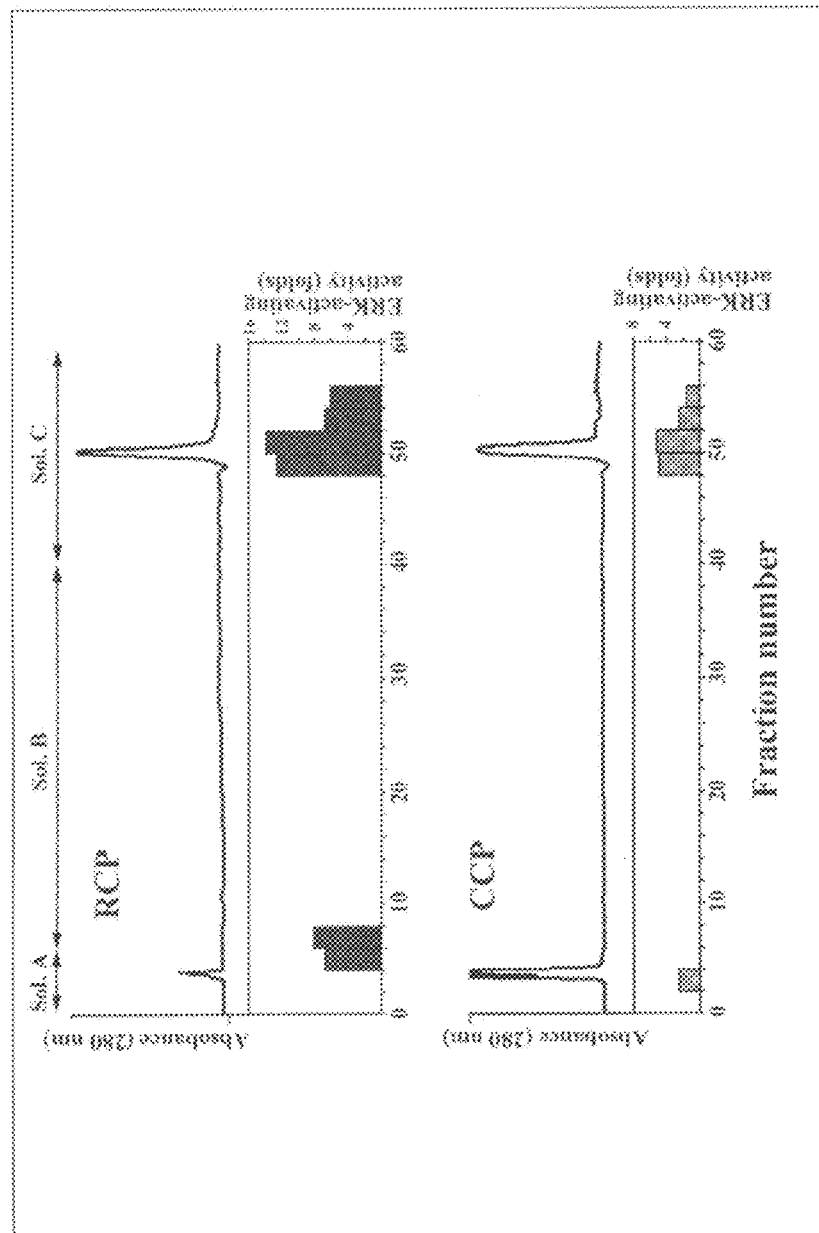
FIG. 1 shows chromatofocusing of reoxygenation-conditioned PBS (RCP; upper panel) and control-conditioned PBS (CCP; lower panel) from cultured cardiac myocytes. Black bars indicate the ERK activating activity of each fraction on cultured cardiac myocytes.

The secreted eIF5A protein of the present invention (hereinafter also referred to as secreted eIF5A) is a novel protein which is secreted extracellularly from a cell exposed to an oxidative stress. Conventional eIF5A is a protein which is said to be produced in the cytoplasm and changed to deoxyhypusinated eIF5A by deoxyhypusine synthase and further to hypusinated eIF5A, an active form, by the action of deoxyhypusine hydroxylase. Furthermore, the action of the hypusinated eIF5A is said to promote translation of mRNA involved in cell proliferation (Amino Acids 2001; 20: 91-104). However, the eIF5A is a protein which is present only in the cytoplasm and was not known to be secreted extracellularly.

The secreted eIF5A of the present invention clearly differs from the eIF5A which is present in the cytoplasm not only in function but also as a substance. Specifically, the isoelectric point of the cytoplasmic eIF5A is 5.5 to 5.4, whereas the isoelectric point of the secreted eIF5A is 5.4 to 5.3. That is, the isoelectric point of the secreted eIF5A is 0.1 lower than the isoelectric point of cytosolic eIF5A.

Furthermore, the secreted eIF5A of the present invention includes an unhypusinated form and a hypusinated form. The isoelectric point of the secreted hypusinated eIF5A is approx. 5.4, which is approx. 0.1 higher than that of the secreted unhypusinated eIF5A. The isoelectric point mentioned herein is a value determined by two-dimensional gel electrophoresis.

More specifically, among the secreted eIF5A proteins of the present invention, the isoelectric point of the secreted unhypusinated eIF5A is approx. 5.3, which is approx. 0.1 lower than that of the cytosolic unhypusinated eIF5A. The isoelectric point of the secreted hypusinated eIF5A is approx. 5.4, which is 0.1 higher than that of the secreted unhypusinated eIF5A.

Between the secreted unhypusinated eIF5A and the secreted hypusinated eIF5A, the secreted hypusinated eIF5A has a higher apoptosis-inducing activity and is particularly preferred.

As the secreted (hypusinated) eIF5A of the present invention is secreted, for example, from cultured cells exposed to a hypoxia/reoxygenation condition, the secreted (hypusinated) eIF5A can be collected from a medium of the cultured cells. The cultured cells used herein are not particularly limited so long as the cells are culturable cells derived from mammals, and examples thereof include cardiac myocytes as well as various established cell lines. Examples of the hypoxia/reoxygenation condition include culturing at an oxygen concentration of lower than 0.1% for 20 to 60 min and after that at a normal oxygen concentration of 20%. After 10 to 15 min of culturing under a reoxygenation condition, the secreted (hypusinated) eIF5A of the present invention can be separated from the culture supernatant.

Furthermore, as the cytosolic (hypusinated) eIF5A has already been cloned, the secreted (hypusinated) eIF5A of the present invention can also be produced by culturing, under a hypoxia/reoxygenation condition, cells transfected with a eIF5A gene by recombinant DNA technology and collecting the eIF5A from the culture supernatant. Here, the nucleotide sequence of the cytosolic eIF5A gene and the amino acid sequence of the cytosolic eIF5A are shown as SEQ ID NO: 1. As the secreted eIF5A of the present invention is also obtained by expressing the gene of the eIF5A, the secreted eIF5A has the amino acid sequence of SEQ ID NO: 1. Furthermore, the secreted eIF5A of the present invention includes polypeptides having an amino acid sequence of SEQ ID NO: 1, in which one or more amino acids are deleted, substituted or added so long as the polypeptides have the same function.

The secreted (hypusinated) eIF5A of the present invention has an apoptosis-inducing action, in particular, an action of inducing apoptosis caused by an oxidative stress. As a cultured cell system containing cytosolic eIF5A did not undergo apoptosis, the apoptosis-inducing ability is specific to the secreted (particularly hypusinated) eIF5A.

Furthermore, the apoptosis-inducing action of the secreted (hypusinated) eIF5A of the present invention involves both a caspase-dependent pathway and a caspase-independent pathway.

As the secreted (hypusinated) eIF5A of the present invention not only induces apoptosis caused by an oxidative stress, but also induces apoptosis under normoxia, it is useful as a preventive or therapeutic agent for cancer, infiltrative diseases (for example, sarcoidosis), and the like.

The pharmaceutical of the present invention can be prepared as a drug product through mixing, dissolution, granulation, tabletting, emulsification, encapsulation, lyophilization, and the like by using the secreted (hypusinated) eIF5A in combination with pharmaceutically acceptable carriers known in the art.

For oral administration, the secreted (hypusinated) eIF5A can be prepared in dosage forms such as a tablet, a pill, a sugar-coated agent, a soft capsule, a hard capsule, a solution, a suspension, an emulsion, a gel, a syrup, and a slurry in combination with pharmaceutically acceptable solvents, diluents, binders, stabilizers, dispersing agents, and the like.

For parenteral administration, the secreted (hypusinated) eIF5A can be prepared in dosage forms such as a solution for injection, a suspension, an emulsion, a cream, an ointment, an inhalant, and a suppository in combination with pharmaceutically acceptable solvents, diluents, binders, stabilizers, dispersing agents, and the like. In the formulation for injection, the secreted (hypusinated) eIF5A can be dissolved in an aqueous solution, preferably a physiologically compatible buffer such as Hanks' solution, Ringer's solution, or a physiological saline buffer. Furthermore, a composition can have forms such as suspension, solution, and emulsion in an oily or aqueous vehicle. Alternatively, a therapeutic agent may be produced in a form of powder, which is to be prepared as an aqueous solution or a suspension before use using sterilized water or the like. For administration by inhalation, the secreted (hypusinated) eIF5A can be powdered in combination with a suitable base material such as lactose or starch, to thereby produce a powder mixture. For the formulation of suppository, the secreted (hypusinated) eIF5A can be mixed with a commonly used suppository base material such as cocoa butter. Furthermore, the therapeutic agent of the present invention can be formulated as a sustained release preparation by encapsulating the secreted (hypusinated) eIF5A in a polymer matrix or the like.

The dose and the number of doses vary depending on the dosage form, the administration route, and the patient's symptom, age, and body weight. Generally, the dose of the secreted (hypusinated) eIF5A is in the range of approx. 0.001 to 1000 mg, preferably approx. 0.01 to 10 mg, per kg body weight per day and can be administered as one dose or divided into several doses per day.

As the secreted (hypusinated) eIF5A of the present invention is secreted from cells under an oxidative stress, the secreted (hypusinated) eIF5A can be used for the diagnosis or determination of oxidative stress. Specifically, the concentration of the secreted (hypusinated) eIF5A in a body fluid or tissue specimen is measured. If the concentration is higher than the concentration under a condition with no oxidative stress, the subject of the body fluid or tissue specimen can be diagnosed as being under an oxidative stress. Furthermore, if the subject is in a treatment for a disease caused by an oxidative stress, whether the course of the treatment is favorable or not can be determined by measuring the concentration of the secreted (hypusinated) eIF5A.

As the secreted (hypusinated) eIF5A, the target of the measurement of the present invention is secreted from cells by an oxidative stress, a specimen is preferably a body fluid and particularly preferably blood, serum, or plasma.

As an embodiment of the diagnosis or the determination of the present invention, immunoassay can be performed by using blood, serum, or plasma obtained from a subject as a sample. Examples of the immunoassay include radioimmunoassay, enzyme immunoassay, fluorescence immunoassay, luminescence immunoassay, immunoprecipitation, immunonephelometry, Western blotting, and immunodiffusion. Enzyme immunoassay is preferred, and enzyme-linked immunosorbent assay (ELISA) (for example, sandwich ELISA) is particularly preferred. The above-mentioned immunoassays, such as ELISA, can be performed by methods known to those skilled in the art.

As an example of the method for diagnosing an oxidative stress using blood, serum, or plasma as a specimen, an anti-secreted (hypusinated) eIF5A antibody (hereinafter referred to simply as anti-eIF5A antibody) is immobilized on a support, a test sample is added thereto, and incubation is performed to allow the anti-eIF5A antibody to bind to the protein. After that, the support is washed, and the secreted (hypusinated) eIF5A protein which binds to the support is detected via the anti-eIF5A antibody.

Examples of the support used for the immobilization of the anti-eIF5A antibody in the present invention include insoluble polysaccharides such as agarose and cellulose, synthetic resins such as silicon resin, polystyrene resin, polyacrylamide resin, nylon resin, and polycarbonate resin, and insoluble supports such as glass and ferrite. These supports can be used in forms such as beads and plates. Beads can be used by filling them in a column or the like. As plates, multiwell plates (96-well multiwell plate etc.), biosensor chips, and the like can be used. Binding of an anti-eIF5A antibody and a support can be performed by usual methods such as chemical bonding and physical adsorption. As all these supports, commercially available ones can be used.

Binding of an anti-eIF5A antibody and the secreted (hypusinated) eIF5A protein in a sample is usually performed in a buffer. Examples of the buffer include phosphate buffer, Tris buffer, citrate buffer, borate buffer, and carbonate buffer, and the usual range of pH is sufficient. Furthermore, the incubation is performed under conditions which have been commonly used, for example, incubation at 4° C. to 37° C. for one to 24 hours. For washing after incubation, any washes can be used so long as the washes do not interfere with binding of the anti-eIF5A antibody and the secreted (hypusinated) eIF5A protein, and examples of the wash include buffers including surfactants such as Tween-20.

In the method of detecting a secreted (hypusinated) eIF5A protein by the present invention, a control sample may be established in addition to a test sample in which the secreted (hypusinated) eIF5A protein is to be detected. Examples of the control sample include negative control samples which do not contain the secreted (hypusinated) eIF5A protein, and positive control samples which contain the secreted (hypusinated) eIF5A protein. In this case, the secreted (hypusinated) eIF5A protein in the test sample can be detected by comparing a result obtained using a negative control sample which does not contain the secreted (hypusinated) eIF5A protein, with a result obtained by using a positive control sample which contains the secreted (hypusinated) eIF5A protein.

Furthermore, the secreted (hypusinated) eIF5A protein contained in a test sample can be quantitatively detected by preparing a series of control samples with concentrations changed stepwise, obtaining a detection result for each control sample as a numerical value, creating a standard curve, and quantifying by using the numerical value of the test sample based on the standard curve.

As a preferred embodiment of detection of a secreted (hypusinated) eIF5A protein which binds to a support via an anti-eIF5A antibody, a method using an anti-eIF5A antibody labeled a labeling substance can be mentioned. For example, a test sample is brought into contact with an anti-eIF5A antibody immobilized on a support, the support is washed, and then a secreted (hypusinated) eIF5A protein is detected using a labeled antibody which specifically recognizes the secreted (hypusinated) eIF5A protein.

The anti-eIF5A antibody can be labeled by commonly known methods. As labeling substances, labeling substances known to those skilled in the art, such as fluorescent dyes, enzymes, coenzymes, chemiluminescent substances, and radioactive substances, can be used. Specific examples of the labeling substances include radioisotopes ($^{32}P$, $^{14}C$, $^{125}I$, $^{3}H$, $^{131}I$, etc.), fluorescein, rhodamine, dansyl chloride, umbelliferone, luciferase, peroxidase, alkaline phosphatase, β-galactosidase, β-glucosidase, horseradish peroxidase, glucoamylase, lysozyme, saccharide oxidase, microperoxidase, biotin, and ruthenium. When biotin is used as a labeling substance, a biotin-labeled antibody is added and then streptavidin binding to an enzyme such as peroxidase is preferably added. To allow a labeling substance to bind to an anti-eIF5A antibody, known methods such as glutaraldehyde methods, maleimide methods, pyridyl disulfide methods, and periodic acid methods can be used.

Specifically, a solution containing an anti-eIF5A antibody is added to a support such as a plate or beads to immobilize the anti-eIF5A antibody on the support. The plate or beads are washed, and then blocking is performed using, for example, BSA, gelatin, or albumin to prevent nonspecific binding of the protein. The support is washed again, and the test sample is added to the plate or the beads. After incubation, the support is washed, and a labeled anti-eIF5A antibody is added. After appropriate incubation, the plate or the beads are washed, and the labeled anti-eIF5A antibody which remains on the support is detected. Detection can be performed by methods known to those skilled in the art. For example, when a radioactive substance is used for labeling, detection can be performed by liquid scintillation or RIA method. When an enzyme is used for labeling, a substrate is added and detection can be performed through an enzymatic change of the substrate, for example, coloration can be detected with an absorption spectrometer. Specific examples of the substrate include 2,2-azino-bis(3-ethylbenzothiazoline-6-sulfonic acid)diammonium salt (ABTS), 1,2-phenylenediamine(ortho-phenylenediamine), and 3,3',5,5'-tetramethylbenzidine (TMB). When a fluorescent substance or a chemiluminescent substance is used, it can be detected with a detection luminometer.

As a particularly preferred embodiment of the method for detecting a secreted (hypusinated) eIF5A protein of the present invention, a method using a biotin-labeled anti-eIF5A antibody and streptavidin can be mentioned.

Specifically, a solution containing an anti-eIF5A antibody is added to a support such as a plate to immobilize the anti-eIF5A antibody thereon. The plate is washed, and then blocking is performed using BSA or the like to prevent nonspecific binding of the protein. The plate is washed again, and a test sample is added to the plate. After incubation, the plate is washed, and then a biotin-labeled anti-eIF5A antibody is added. After suitable incubation, the plate is washed, avidin which binds to an enzyme such as alkaline phosphatase or peroxidase is added. After incubation, the plate is washed, a substrate for the enzyme which binds to avidin is added, and the secreted (hypusinated) eIF5A protein is detected by using an enzymatic change of the substrate or the like as an indicator.

As another embodiment of the method for detecting a secreted (hypusinated) eIF5A protein of the present invention, a method using one or more primary antibodies which specifically recognize a secreted (hypusinated) eIF5A protein and one or more secondary antibodies which specifically recognize the primary antibodies can be mentioned.

For example, a test sample is brought into contact with one or more anti-eIF5A antibodies immobilized on a support and incubated, then the support is washed, and, after wash, a secreted (hypusinated) eIF5A protein bound is detected by using primary anti-eIF5A antibodies and one or more secondary antibodies which specifically recognize the primary antibodies. In this case, the secondary antibodies are preferably labeled with a labeling substance.

As another embodiment of the method for detecting a secreted (hypusinated) eIF5A protein of the present invention, a method using an agglutination reaction can be mentioned. In this method, a secreted (hypusinated) eIF5A protein can be detected by using an anti-eIF5A antibody-sensitized carrier. Any antibody-sensitized carriers can be used so long as the carriers are insoluble, do not cause a nonspecific binding reaction, and are stable. Examples of the antibody-sensitized carrier include latex particles, bentonite, collodione, kaolin, and immobilized sheep erythrocytes, and latex particles are preferably used. Examples of the latex particles include polystyrene latex particles, styrene-butadiene copolymer latex particles, and polyvinyltoluene latex particles, and polystyrene latex particles are preferably used. Sensitized particles are mixed with a sample, and the mixture is stirred for a predetermined time. As the degree of agglutination of particles is greater when a higher concentration of a secreted (hypusinated) eIF5A protein is contained in the sample, the secreted (hypusinated) eIF5A protein can be detected by observing agglutination macroscopically. Furthermore, the secreted (hypusinated) eIF5A protein can also be detected by measuring turbidity due to agglutination with a spectrophotometer or the like.

As another embodiment of the method for detecting the protein of the present invention, for example, a method using a biosensor which utilizes a surface plasmon resonance phenomenon can be mentioned. A biosensor utilizing a surface plasmon resonance phenomenon enables observation of a protein-protein interaction in real time as a surface plasmon resonance signal by using a trace amount of proteins without labeling. For example, each binding of an anti-eIF5A antibody and a secreted (hypusinated) eIF5A protein can be detected by using a biosensor such as BIAcore (Biacore International AB). Specifically, a test sample is brought into contact with a sensor chip on which an anti-eIF5A antibody is immobilized, each secreted (hypusinated) eIF5A protein binding to the anti-eIF5A antibody can be detected as a change in the resonance signal.

The detection method of the present invention can also be automated using various automatic test apparatus, and thus a large amount of samples can be tested at a time.

The agent for diagnosing an oxidative stress of the present invention may be provided in the form of a kit. The diagnostic agent for an oxidative stress of the present invention contains at least an anti-eIF5A antibody. When the diagnostic agent is based on EIA such as ELISA, a carrier which solidifies an antibody may be contained, or an antibody may be allowed to bind to a carrier beforehand. When the diagnostic agent is based on agglutination using a carrier such as latex, a carrier to which an antibody is adsorbed may be contained. Furthermore, the diagnostic agent may suitably contain a blocking solution, a reaction solution, a reaction terminating solution, a reagent for treating a sample, and the like.

The anti-eIF5A antibody used in the diagnostic agent of the present invention may be one binding specifically to each secreted (hypusinated) eIF5A protein, regardless of the origin, the type (monoclonal or polyclonal), and the shape of the anti-eIF5A antibody. Specifically, known antibodies such as mouse antibodies, rat antibodies, avian antibodies, human antibodies, chimera antibodies, and humanized antibodies can be used. Antibodies may be polyclonal antibodies, but monoclonal antibodies are preferred. Commercially available antibodies may be used so long as the antibodies can be measured specifically with high sensitivity.

Furthermore, an anti-eIF5A antibody immobilized on a support and an anti-eIF5A antibody labeled with a labeling substance may recognize the same epitope of a secreted (hypusinated) eIF5A protein, but different epitopes are preferably recognized, and sites are not particularly limited.

Anti-eIF5A antibodies used in the present invention can be obtained using known means as polyclonal or monoclonal antibodies. As the anti-eIF5A antibodies used in the present invention, mammal-derived or avian-derived monoclonal antibodies are preferred. Mammal-derived monoclonal antibodies are particularly preferred. Mammal-derived monoclonal antibodies include antibodies produced by using hybridoma and antibodies produced by using a host transfected with an expression vector having an antibody gene through genetic engineering technique.

Monoclonal antibody-producing hybridoma can be prepared basically by using known techniques as follows. Specifically, a secreted (hypusinated) eIF5A protein is used as a sensitizing antigen and immunized by using the antigen according to a usual immunological method, the obtained immunocyte is fused with a known parent cell by a usual cell fusion method, and screening a monoclonal antibody-producing cell by a usual screening method, to thereby obtain the hybridoma.

Specifically, a monoclonal antibody can be prepared as follows.

A purified secreted (hypusinated) eIF5A protein is used as a sensitizing antigen. Alternatively, a partial peptide of the secreted (hypusinated) eIF5A protein can also be used as a sensitizing antigen. At this time, the partial peptide can be obtained based on the amino acid sequence of a human secreted (hypusinated) eIF5A protein by chemical synthesis, by incorporating a part of the human eIF5A gene into an expression vector, or by degrading a natural human secreted (hypusinated) eIF5A protein by a proteolytic enzyme. The portion and the size of the human secreted (hypusinated) eIF5A protein used as a partial peptide are not limited.

Mammals immunized with a sensitizing antigen are not particularly limited, but are preferably selected in view of the compatibility with a parent cell used for cell fusion. Generally, rodents such as mice, rats and hamsters, birds, rabbits, monkeys, and the like are used.

Animals are immunized with a sensitizing antigen according to known methods. For example, as a common method, a sensitizing antigen is injected to mammals intraperitoneally or subcutaneously. Specifically, a sensitizing antigen is diluted with PBS (phosphate-buffered saline), physiological saline, or the like and suspended in an appropriate volume, mixed with an appropriate amount of a usual adjuvant such as Freund's complete adjuvant, as required, emulsified, and then administered to mammals several times every 4 to 21 days. Furthermore, an appropriate carrier can also be used at the time of immunization with a sensitizing antigen. In particular, when a partial peptide with a low molecular weight is used as a sensitizing antigen, the partial peptide is preferably allowed to bind to a carrier protein such as albumin or keyhole limpet hemocyanin and used for immunization.

After a mammal is thus immunized, and the elevation of the level of a required antibody in serum is confirmed, immunocytes are collected from the mammal and subjected to cell fusion. Particularly preferred examples of immunocytes include splenic cells.

As the other parent cell fused with the immunocyte, a mammal myeloma cell is used. Preferred examples of the myeloma cell include various known cell strains, for example, P3 (P3×63Ag8.653) (J. Immnol. [1979] 123, 1548-1550), P3×63Ag8U.1 (Current Topics in Microbiology and Immunology [1978] 81, 1-7), NS-1 (Kohler. G. and Milstein, C. Eur. J. Immunol. [1976] 6, 511-519), MPC-11 (Margulies. D. H. et al., Cell [1976] 8, 405-415), SP2/0 (Shulman, M. et al., Nature [1978] 276, 269-270), FO (de St. Groth, S. F. et al., J. Immunol. Methods [1980] 35, 1-21), 5194 (Trowbridge, I. S. J. Exp. Med. [1978] 148, 313-323), and 8210 (Galfre, G. et al., Nature [1979] 277, 131-133).

The immunocytes and myeloma cells can be fused basically by known methods, for example, the method of Kohler, Milstein, et al. (Kohler. G. and Milstein, C., Methods Enzymol. [1981] 73, 3-46).

More specifically, the cell fusion is carried out in a usual nutrient culture broth in the presence of, for example, a cell fusion promoter. Examples of the fusion promoter include polyethylene glycol (PEG) and Sendai virus (HVJ). To increase fusion efficiency as required, aids such as dimethyl sulfoxide can be further added for use.

The ratio of an immunocyte and a myeloma cell used can be arbitrarily selected. For example, the ratio of an immunocyte to a myeloma cell is preferably 1 to 10. Examples of the culture broth used for the cell fusion include RPMI 1640 culture broth suitable for proliferation of the myeloma cell strains, MEM culture broth, and other usual culture broths used for this type of cell culture. Serum replacement fluids such as fetal calf serum (FCS) can also be used in combination.

For cell fusion, a target fused cell (hybridoma) is formed by mixing predetermined amounts of the immunocyte and myeloma cell well in the culture broth, adding PEG solution (for example, an average molecular weight of approx. 1000 to 6000) heated at approx. 37° C. beforehand usually at concentration a of 30 to 60% (w/v), and mixing well. Subsequently, an appropriate culture broth is serially added, and the mixture is centrifuged to remove the supernatant. By repeating this procedure, cell fusing agents or the like which are undesirable for proliferation of hybridoma and the like are removed.

The hybridoma thus obtained is selected by culturing the cells in a usual selective culture broth, for example, HAT culture broth (culture broth containing hypoxanthine, aminopterin, and thymidine). The culture in the HAT culture broth is continued for a sufficient time (normally, several days to several weeks) to kill cells (non-fused cells) other than the target hybridoma. Subsequently, hybridoma which produces a target antibody is subjected to screening and single cloning by a usual limiting dilution method.

Screening and single cloning of the target antibody can be carried out by a screening method based on known antigen-antibody reactions. For example, an antigen is allowed to bind to a carrier such as beads made of polystyrene or the like or a commercially available 96-well microtiter plate and reacted with the culture supernatant of hybridoma, the carrier is washed, and then whether or not a target antibody which reacts with the sensitizing antigen in the culture supernatant is contained can be determined by allowing an enzyme-labeled secondary antibody or the like to react. The hybridoma which produces the target antibody can be cloned by a limiting dilution method or the like. At this time, the antigen used for immunization can be used as the antigen.

The hybridoma producing a monoclonal antibody which is thus prepared can be subcultured in a usual culture broth and stored in liquid nitrogen for a long period.

To obtain a monoclonal antibody from the hybridoma, a method of culturing the hybridoma according to a usual method and obtaining as the culture supernatant or a method of administering the hybridoma to a compatible mammal to proliferate it and obtaining the antibody as ascites can be used. The former method is suitable to obtain high-purity antibodies, while the latter method is suitable for mass production of antibodies.

Antibodies used in the present invention are not limited to the whole antibody molecules and may be fragments or modified fragments of an antibody so long as the antibodies bind to the secreted (hypusinated) eIF5A protein. Both bivalent antibodies and univalent antibodies are also included. Examples of the fragments of an antibody include Fab, F(ab')2, Fv, Fab/c containing one Fab and complete Fc, and single-chain Fv (scFv) to which Fv of the H chain or the L chain is linked with an appropriate linker. Specifically, an antibody is treated with an enzyme such as papain or pepsin to produce an antibody fragment, or the gene coding for the antibody fragment is constructed, and the gene is introduced into an expression vector and expressed in an appropriate host cell (for example, refer to Co, M. S. et al., J. Immunol. [1994] 152, 2968-2976; Better, M. & Horwitz, A. H., Methods in Enzymology [1989] 178, 476-496, Academic Press, Inc.; Plueckthun, A. & Skerra, A., Methods in Enzymology [1989] 178, 476-496, Academic Press, Inc.; Lamoyi, E., Methods in Enzymology [1989] 121, 652-663; Rousseaux, J. et al., Methods in Enzymology [1989] 121, 663-669; and Bird, R. E. et al., TIBTECH [1991] 9, 132-137).

scFv can be obtained by linking the V region of H chain and the V region of light (L) chain of an antibody. In this scFv, the V region of H chain and the V region of L chain are linked with a linker, preferably with a peptide linker (Huston, J. S. et al., Proc. Natl. Acad. Sci. U.S.A. [1988] 85, 5879-5883). The V region of H chain and the V region of L chain in scFv may be derived from any antibodies described in the present specification. Examples of the peptide linker for linking the V regions include arbitrary single-stranded peptides including 12 to 19 amino acid residues.

DNA coding for scFv can be obtained by PCR amplification by using, as a template, a whole sequence of DNA coding for the H chain or the V region of H chain and DNA coding for the L chain or the V region of L chain in the antibody, or a DNA portion coding for a required amino acid sequence and a primer pair which defines the both ends of the DNA, and further amplification by using DNA coding for a peptide linker portion and a primer pair which defines the linker so that the both ends should be linked to the H chain and the L chain.

Furthermore, once DNA coding for scFv is prepared, an expression vector containing the DNA and a host transformed with the expression vector can be obtained by a usual method. scFv can be obtained by a usual method using the host.

Fragments of the antibody can be expressed by using the obtained genes as described above and produced by the host. The "antibodies" in the present invention include the antibody fragments.

As modified antibodies, anti-eIF5A antibodies which bind to various molecules such as labeling substances can also be used. The "antibodies" in the present invention also include the modified antibodies. The modified antibodies can be obtained by subjecting the obtained antibodies to chemical modification. It is noted that methods for modifying antibodies have already been established in the art.

Furthermore, antibodies used in the present invention may be bispecific antibodies. Bispecific antibodies may be bispecific antibodies having antigen-binding sites which recognize different epitopes on a molecule, or one having one antigen-binding site which may recognize a secreted (hypusinated) eIF5A protein and the other antigen-binding site which may recognize a labeling substance or the like. The bispecific antibody can be prepared by linking pairs of the H regions and the L regions of two antibodies or obtained by fusing hybridomas producing different monoclonal antibodies to prepare a fusion cell which produces a bispecific antibody. Furthermore, bispecific antibodies can also be prepared by genetic engineering techniques.

As the secreted (hypusinated) eIF5A of the present invention induces apoptosis caused by an oxidative stress, an agent for inhibiting the secreted (hypusinated) eIF5A can be used as an apoptosis inhibitor. Examples of the secreted (hypusinated) eIF5A inhibitor include anti-eIF5A neutralizing antibodies. The origin, type (monoclonal or polyclonal) and the shape of anti-eIF5A neutralizing antibodies are not limited. Specific examples of the anti-eIF5A neutralizing antibodies include known antibodies such as mouse antibodies, rat antibodies, avian antibodies, human antibodies, chimera antibodies, and humanized antibodies. Antibodies may be polyclonal antibodies, but monoclonal antibodies, which can be mass-produced, are preferred in view of administration into a living body. It is sufficient that the secreted (hypusinated) eIF5A can be neutralized in the living body to inhibit the action of the secreted (hypusinated) eIF5A.

Here, as the apoptosis inhibitor of present invention inhibits apoptosis caused by an oxidative stress, the apoptosis inhibitor of present invention is useful as an preventive or therapeutic agent for various diseases caused by an oxidative stress, such as, for example, not only ischemia-reperfusion injury and ultraviolet ray/radiation damage, but also atherosclerosis, aging, and the like, which are accelerated by an oxidative stress. Examples of "ischemic" diseases include ischemic heart diseases (angina pectoris and acute myocardial infarction), cerebral infarction, lung thromboembolism, ischemic intestinal diseases (acute mesenteric arterial occlusion and ischemic colitis), renal embolism, and cases of heart arrest in heart transplantation, open-heart surgery, and the like using an artificial heart-lung apparatus.

The pharmaceutical of the present invention can be prepared as a drug product by mixing, dissolution, granulation, tableting, emulsification, encapsulation, lyophilization, or the like of a secreted (hypusinated) eIF5A inhibitor with a pharmaceutically acceptable carrier known in this technical field.

For oral administration, the secreted (hypusinated) eIF5A inhibitor can be prepared in dosage forms such as a tablet, a pill, a sugar-coated agent, a soft capsule, a hard capsule, a solution, a suspension, an emulsion, a gel, a syrup, and a slurry with pharmaceutically acceptable solvents, diluents, binders, stabilizers, dispersing agents, and the like.

For parenteral administration, the secreted (hypusinated) eIF5A inhibitors can be prepared as a drug product in dosage forms such as a solution for injection, a suspension, an emulsion, a cream, an ointment, an inhalant, and a suppository in combination with pharmaceutically acceptable solvents, diluents, binders, stabilizers, dispersing agents, and the like. In the formulation for injection, the secreted hypusinated eIF5A inhibitor can be dissolved in an aqueous solution, preferably in a physiologically compatible buffer such as Hanks' solution, Ringer's solution, or physiological saline buffer. Furthermore, a composition can be in forms such as suspension, solution, or emulsion in an oily or aqueous vehicle. Alternatively, a therapeutic agent may be produced in a form of powder, and an aqueous solution or a suspension may be prepared with sterilized water before use. For administration by inhalation, the secreted hypusinated eIF5A inhibitor is powdered, and a powder mixture can be prepared with a suitable base material such as lactose or starch. Suppository can be produced by mixing the secreted (hypusinated) eIF5A inhibitor with a commonly used suppository base material such as cocoa butter. Furthermore, the therapeutic agent of the present invention can be encapsulated in a polymer matrix or the like and formulated as a sustained release preparation.

The dose and the number of doses vary depending on the dosage form, the administration route, and the patient's symptom, age, and body weight. Generally, the secreted (hypusinated) eIF5A inhibitor in the range of approx. 0.001 to 1000 mg, preferably approx. 0.01 to 10 mg, per kg body weight per day, can be administered as one dose or the dose can be divided into several times per day. As acute phase treatment of acute myocardial infarction, cerebral infarction, and the like, reperfusion therapy for reopening the occluded vessel using a thrombolytic agent (urokinase, tissue plasminogen activation factor [tPA], etc.) or a balloon catheter is generally performed in the early phase of the disease. The anti-(secreted) eIF5A neutralizing antibody can be intravenously (as one shot) administered before or during reperfusion (if possible, 5 to 10 min before). When an occluded vessel is expanded with a balloon catheter and a stent is inserted, the anti-(secreted) eIF5A neutralizing antibody can be similarly administered before or during reperfusion (vascular dilatation). In a drug delivery balloon catheter, the anti-(secreted) eIF5A neutralizing antibody is preferably administered before or during blood reflow by vascular dilatation.

EXAMPLES

The present invention will be described in detail with reference to the following examples. However, the scope of the present invention is not limited to these examples.

First, the experimental methods will be described.
(Cells Culture)

According to the description in Circ. Res. 78, 82-90 (1996), a primary culture of ventricular cardiac myocytes was prepared from neonatal rats. These cells were cultured for 2 days until they were confluent.
(Hypoxia and Reoxygenation)

According to the description in Circ. Res. 78, 82-90 (1996), a hypoxia condition ($N_2$ 95%, $CO_2$ 5%, and $O_2$<0.1%) was achieved. After incubating in a hypoxic condition for 60 min (for cardiac myocytes) or 20 min (for quail muscle cells), the cells were reoxygenated by immediately replacing the hypoxic PBS with normoxic PBS for 10 min. The supernatant PBS was collected after 10 min of reoxygenation as reoxygenation-conditioned PBS (RCP). Also the supernatant PBS was collected after 10 min of incubation with non-stimulated cardiac myocytes under normoxia as control-conditioned PBS (CCP). The RCP and CCP were concentrated and the fractions of molecular weight>10 kD were collected by using centripreps (YM-10; Millipore Corporation).

(Chromatofocusing)

Both RCP and CCP were collected from the same number of cells, loaded onto a MONO-P (5 mm×200 mm) column (GE Healthcare) connected to a GILSON HPLC system at a flow rate of 1 ml min$^{-1}$, equilibrated with Solution A (0.025M BisTris, pH 7.1), eluted with Solution B (10% Poly Buffer74, pH4.0), and washed out the column-bound components with Solution C (1M NaCl/10% Poly Buffer74, pH 4.0).

(Cloning and Plasmid Construction)

Human eIF5A cDNA was amplified by RT-PCR from total RNA isolated from SaSO2 cells (human osteoblast-like cell line) and subcloned into the EcoRI/Xho I site of pcDNA4/myc-His Vector (Invitrogen). Then, FLAG plus His-tagged eIF5A construct was generated with the following primers.

The forward primer was

```
                                              (SEQ ID NO: 2)
5'-CACCGAATTCAAAATGGCAGATGACT-3',
``` and the reverse primer was

```
                                              (SEQ ID NO: 3)
5'-ATATACTCGAGTCAGTGATGGTGATGGTGGTGCTTGTCATC

GTCGTCCTTGTAA TCTTTTGCCATGGCCTTGATTG-3'
```

Then the construct was subcloned into pcDNA3.1 Directional TOPO Vector (Invitrogen).

(Recombinant eIF5A Protein)

Flag plus His-tagged eIF5A and mutant eIF5A (K50A) were transiently expressed in a quail muscle cell line (clone CRL-1962, ATCC) with FuGENE HD Transfection Reagent (Roche). After 48 hours of transfection, the cells were subjected to hypoxia for 20 min followed by reoxygenation for 10 min. The reoxygenated PBS were collected and concentrated, and then the recombinant proteins were purified with Ni-NTA Purification System (Invitrogen; according to the manufacture's instruction). Cytosolic recombinant eIF5A was also collected from transfected cells under a native condition (normoxia).

(Polyclonal Anti-eIF5A Antibody)

Rabbit anti-eIF5A polyclonal antibodies (J-M) and (J-C) were generated against human eIF5A peptide (amino acid residues 38 to 57, which include the hypusination site, and amino acid residues 138 to 154, respectively; coupled to keyhole limpet hemocyanin).

(Western Blot Analysis of Cultured Cardiac Myocytes)

Cultured cardiac myocytes were treated with the recombinant eIF5A (RCP) for 5 min, the medium was immediately aspirated, and the cells were frozen with liquid nitrogen. As described elsewhere, the cells were lysed with buffer A on ice, and the cell lysate was centrifuged. The supernatant was suspended in Lemli's sample buffer. A portion of the sample was subjected to Western blot analysis by using rabbit polyclonal phosphospecific anti-ERK1/2 (Thr202/Tyr204) antibody (Cell Signaling, Inc.). Another portion of the same sample was subjected to Western blot analysis by using rabbit polyclonal control anti-ERK1/2 antibody (Cell Signaling, Inc.). The antibody-antigen complex was colored by a chemiluminescence system using alkaline phosphatase (New England Biolabs, Inc.).

(Immunofluorescence)

Immunofluorescence staining of cultured cardiac myocytes and myocardial tissue were performed by Tyramide Signal Amplification (TSA) technology for fluorescence (TSA™ Biotin System, NEN Life Science Products, PerkinElmer; according to the manufacture's instruction). Double immunostaining for cardiac myosin was performed according to the same procedure as described in Biochem. Biophys. Res. Commun. 317, 162-168 (2004).

(Immunoelectron Microscopy)

Cultured cardiac myocytes were subjected to hypoxic condition for 60 min followed by reoxygenation for 10 min, fixed in 4% paraformaldehyde for 2 hours, washed with PBS, and dehydrated in a graded series (50 to 100%) of cold ethanol. The cells were embedded in LR White Resin (Nisshin EM, Co. Ltd., Japan)/100% ethanol (1:1) for 2 hours, then embedded in pure LR White Resin, and polymerized under ultraviolet light irradiation at 4° C. overnight. Ultrathin sections were prepared, blocked with 1% bovine serum albumin in PBS and incubated with anti-eIF5A antibody (J-M) overnight. The section was washed in PBS, incubated with Protein A conjugated gold colloidal particles-20 nm (EY Laboratories, Inc.) and then examined with an electron microscope (H-7000, HITACHI, Japan).

(Electron Microscopy)

The cardiac myocytes were treated with recombinant eIF5A for a predetermined period. The cells were fixed in 2% glutaraldehyde, postfixed in 2% osmium tetraoxide, dehydrated in ethanol, and embedded in a resin. Ultrathin section were prepared, stained with uranyl acetate and lead citrate, and examined with an electron microscope (H-7000, HITACHI, Japan).

(Terminal Deoxynucleotidyl Transferase Nick-End Labeling (TUNEL) Staining)

TUNEL staining was performed with In Situ Apoptosis Detection Kit (TAKARA BIO Inc., Shiga, Japan; according to the manufacture's instruction), and then a diaminobenzidine (DAB) reaction was carried out. To distinguish cardiac myocytes from non-muscle cells, cells were incubated with mouse anti-cardiac myosin mAb (clone CMA19) and alkaline phosphatase-labeled anti-mouse IgG antibody (Santa Cruz Biotechnology, Inc.) and then reacted with a substrate (alkaline phosphatase substrate kit III, Vector Laboratories, Inc.), which produces a blue reaction product.

(Analysis of Subcellular Localization of Apoptosis Inducing Factor (AIF) in Cultured Cardiac Myocytes)

Tyramide Signal Amplification (TSA) technology was used for fluorescence (TSA™ Biotin System, NEN Life Science Products, PerkinElmer; according to the manufacture's instruction). Cardiac myocytes were treated with a recombinant eIF5A (RCP) for a predetermined time and fixed with 4% paraformaldehyde in PBS for 15 min. The cells were washed with PBS and then incubated with rabbit anti-AIF mAb (E20; Epitomics Inc.) for 1 hour. The cells were washed, then incubated with biotinylated anti-rabbit IgG antibody (Chemicon International, Inc.) for 1 hour, washed, and incubated with streptavidin-horseradish peroxidase (Vector) for 30 min. The cells were washed in TNT buffer (0.1 M Tris-HCl, pH 7.5, 0.15 M NaCl, 0.05% Tween 20) and then incubated with biotinylated-tyramide for appropriate time (3 to 10 min). The cells were washed in TNT buffer and then incubated with FITC-labeled avidin-D (Vector) for 30 min. Nuclei were stained with 1 μg·mL$^{-1}$ Hoechst 33342 (DOJINDO Laboratories, Kumamoto, Japan). Confocal laser microscopy was performed on LSM510 Laser Scanning Microscope (Zeiss).

(Analysis of Release of Cytochrome c from Mitochondria)

Cultured cardiac myocytes were treated with a recombinant eIF5A for a predetermined time. Nucleic, mitochondrial, and cytosolic fraction of the cells were prepared as described in Non Patent Literatures 1 and 2. Briefly, $3 \times 10^6$ cells were washed in PBS, and suspended in 250 µl of a lysis buffer (250 mM sucrose, 50 mM Pipes/KOH, pH7.4, 50 mM KCl, 5 mM EGTA, 2 mM $MgCl_2$, 1 mM DTT, and 1 mM PMSF). After 30 min on ice, the cells were lysed with 40 strokes using pestle B in a Dounce homogenizer, and centrifuged at 80 g for 10 min. The pellets were collected as the nucleic fraction. Then, the supernatants were prepared from cell lysates by centrifugation at 20,000 g for 20 min. The pellets were collected as the mitochondrial fraction, and the supernatants were regarded as the cytosolic fraction. The nucleic, mitochondrial, and cytosolic fractions were subjected to Western blot analysis with rabbit anti-AIF mAb (E20; Epitomics Inc., CA, USA) or mouse anti-cytochrome c mAb (7H8.2C12; Lab Vision Corp., CA, USA). The antibody-antigen complexes were developed with a chemiluminescence system using alkaline-phosphatase (New England Biolabs, Inc.).

(Annexin V-Staining of Cultured Cardiac Myocytes)

Cardiac myocytes were treated with a recombinant eIF5A (RCP) for a predetermined time. The cells were incubated with biotinylated-annexin V in 1× binding buffer (Annexin V-Biotin Apoptosis Detection Kit, BioVision Inc.) for 5 min and then fixed with 2% paraformaldehyde in PBS for 15 min. After washing in PBS, the cells were incubated with streptavidin-horseradish peroxidase (Vector) for 30 min. The subsequent procedures for immunofluorescence by TSA technology were the same as for AIF. To distinguish cardiac myocytes from non-muscle cells, cells were further incubated with mouse anti-cardiac myosin (clone CMA19) mAb (Non Patent Literature 1), followed by incubation with tetramethyl rhodamine isothiocyanate (TRITC)-conjugated anti-mouse IgG antibody, and then photographed in a fluorescence microscope.

(Ischemia and Reperfusion)

Rats (male, 250 to 280 g) were subjected to coronary artery ligation according to J. Pathol. 180, 305-310 (1996). Briefly, rats were anesthetized with sodium pentobarbital (40 mg $Kg^{-1}$, intraperitoneally), intubated, and ventilated with room air (tidal volume, 20 ml/Kg, 60 min) with a respirator (SN-480-7, Shinano Manufacturing Co., Ltd., Tokyo, Japan). After lateral thoracotomy and pericardiectomy, a 6-0 silk stitch was placed near the intramyocardial location of the left coronary artery beneath the left atrial appendage. Coronary artery occlusion was performed by pressing a short length of tube over the ends of the suture and clamping it firmly against the heart. Reperfusion was achieved by removing the clamp. The standard limb lead II electrocardiogram was monitored continuously. The ischemia and reperfusion of the regional myocardium were confirmed by following the changes of the ST segment level on the electrocardiogram and observing the change in the color of the myocardium.

(Immunohistochemistry)

Rats were slaughtered at each of time point after myocardial ischemia/reperfusion. Cryostat sections (6-µm thick) of heart ventricle were prepared, air-dried, and fixed in acetone for 5 min. The sections were incubated with rabbit polyclonal anti-eIF5A antibody (J-M) at 37° C. for 1 hour, and then incubated with biotinylated anti-rabbit IgG antibody (Vector Laboratories, Inc., CA) at 37° C. for 1 hour. The subsequent procedures by TSA technology for immunofluorescence were similar to the procedures for annexin V.

(Immunocytochemistry)

To distinguish cardiac myocytes from non-muscle cells, double-staining was performed for cardiac myosin and eIF5A with mouse anti-cardiac myosin (CMA19) mAb followed by incubation with TRITC-conjugated anti-mouse IgG antibody as for Annexin V. The procedure for staining of eIF5A was the same as the procedure for tissue samples.

(Two-Dimensional Electrophoresis of myc- and FLAG-Tagged Recombinant eIF5A Protein)

Quail muscle cells were transfected with eIF5A-myc-His vector and myc- and His-tagged recombinant eIF5A protein was collected from the cytoplasm of the transfected cells. Similarly, quail muscle cells were transfected with the eIF5A-FLAG-His vector, the cells were incubated in hypoxia/reoxygenation-conditioned PBS (RCP), and a FLAG- and His-tagged recombinant eIF5A protein was collected from the culture supernatant. The proteins were treated with Ni-NTA Purification System (Invitrogen), and after that gel filtration was performed with phosphate buffer containing 0.15 M NaCl (pH 7.4) using Superdex 200™ 10-300GL (GE Healthcare, 1.0×30 cm, bed capacity 24 mL) to purify the myc- and FLAG-tagged recombinant eIF5A proteins. The first dimensional isoelectric focusing was performed with Immobiline DryStrip (pH 4 to 7, GE Healthcare) which had been allowed to swell overnight with a sample dissolved in 7 M urea, 2 M thiourea, 4% CHAPS, 65 mM dithioerythritol [DTE], 2% IPG buffer pH 4 to 7 (GE Healthcare) and bromophenol blue [BPB]. The electrophoresis was performed at a voltage of 30 V for 7 hours, at 60V for 7 hours, at 60 to 200 V for 30 min, at 200 to 500 V for 30 min, at 500 to 1000 V for 30 min, at 1000 to 8000 V for 30 min, and at 8000 V for 2 hours (19.4 kVh in total). The second dimensional SDS-PAGE was performed with a gel (concentrated gel 4% acrylamide, 2.6% piperazine diacrylamide [PDA], separating gel 12% acrylamide, 2.6% PDA) and the electrophoresis was performed at 12 mA for 2 hours. The gel was transferred to a PVDF membrane, and then the myc- and FLAG-tagged recombinant eIF5A proteins were analyzed by Western blotting. First, the proteins were analyzed using anti-myc monoclonal antibody (Invitrogen), biotinylated anti-mouse IgG antibody and Vectastain ABC-AP Kit (Vector) and then detected with alkaline phosphatase and chemiluminescence. Then, the proteins were analyzed using anti-FLAG monoclonal antibody (M2, Sigma) and horseradish peroxidase (HRP)-labeled anti-mouse IgG antibody and detected with Konica Immunostain HRP-1000 Kit (Konica Corporation).

(Apoptosis Induction in Various Cancer Cells by Recombinant eIF5A)

Quail muscle cells (ATCC; CRL-1962), HeLa cells, human hepatocellular carcinoma cells (ATCC; HB-8064), and human glioblastoma cells (ATCC; CRL-1690) were incubated on a culture slide (BD Falcon) until they were confluent. These cells were treated with a recombinant eIF5A (10 µg/ml) for a predetermined time and fixed. Terminal deoxynucleotidyl transferase nick-end-labeled (TUNEL) staining was performed in situ with an Apoptosis Detection Kit (Takara Bio Inc.).

Example 1

Identification of Humoral Factor Secreted from Hypoxia/Reoxygenation-Conditioned Cultured Cells (1) To identify an apoptosis-inducting humoral factor derived from hypoxia/reoxygenation-conditioned media, fractions having a relative molecular weight ($M_r$) of higher than 10 kD were collected from the supernatant PBS of cardiac myocytes, which were subjected to hypoxia for 60 min and then reoxygenation for 10 min, as reoxygenation-conditioned PBS (RCP) and concentrated.

This is because these fractions have an ERK activation activity and an apoptosis-inducing activity.

Furthermore, supernatant PBS incubated together with non-stimulated cardiac myocytes under normoxia for 10 min was collected as control-conditioned PBS (CCP) and concentrated. Proteins in RCP and CCP were separated by chromatofocusing (FIG. 1).

Figure 2A:
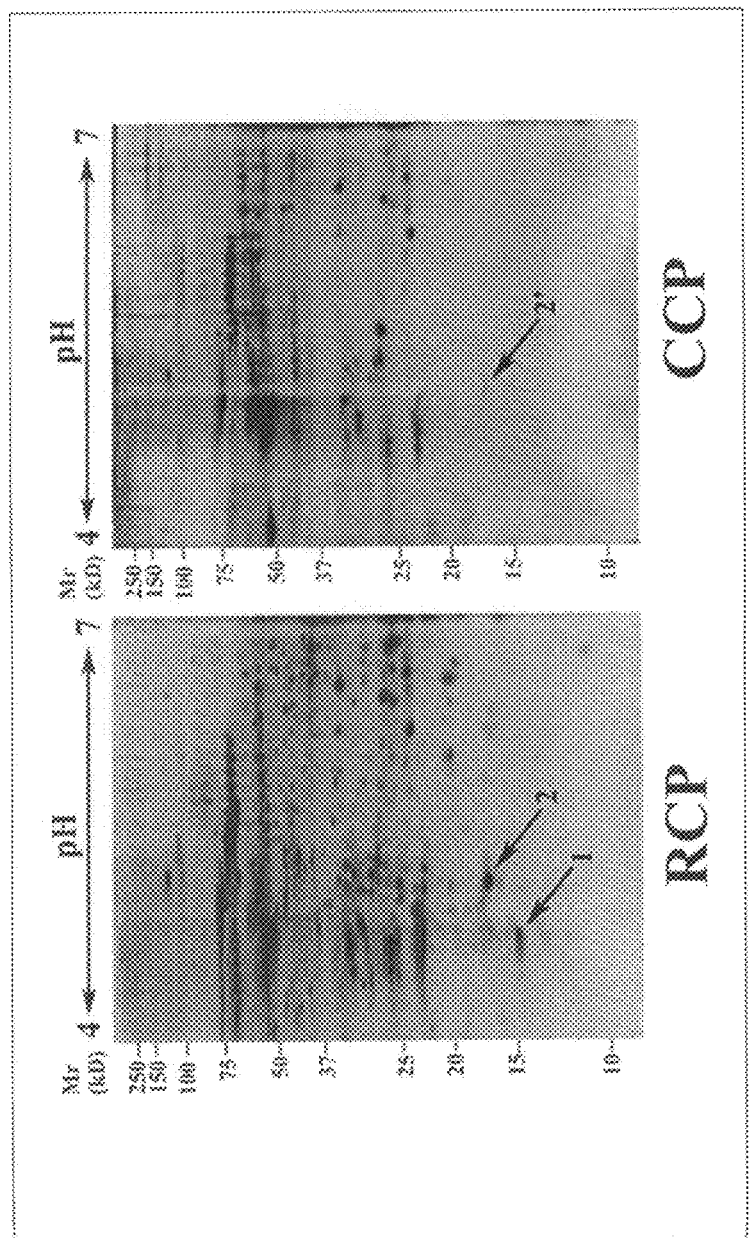
FIG. 2a shows two-dimensional gel electrophoresis of active fractions (fractions 49 to 52) from RCP (left panel) and CCP (right panel) stained with silver. Arrows in RCP (left panel) indicate protein spots (1 and 2). Of these, a spot corresponding to the protein spot 1 is not present in CCP (right panel). Only a small spot (2') corresponding to 2 is present in CCP (right panel).

(2) The ERK-activation activity of each of fractions, which seemed to be one of the most sensitive markers of the target factor, was monitored using cultured rat cardiac myocytes by Western blotting with phosphor-specific anti-ERK1/2 antibody (Cell Signaling Technology, Inc.). Then it was found that fractions 49 to 52 (high-salt [1M NaCl] fractions) in both RCP and CCP groups had strong activity (activity: RCP>CCP; FIG. 1), and fractions 5 to 8 (which were passed through fractions) in RCP had a weak to moderate activity but much less than that of the fractions 49 to 52. Then, the most active fractions (49 to 52) in each group were subjected to two-dimensional electrophoresis (FIG. 2a: left panel, RCP; right panel, CCP). As the active components were not eluted by Solution B, the components are considered acidic. Among spots with low pI values, spot 1 ($M_r$ 14.4 kD and pI 4.8) indicated by an arrow in RCP (FIG. 2a, left panel) was not present in CCP (FIG. 2a, right panel), and spot 2 ($M_r$ 16.8 kD and pI 5.1) indicated by an arrow are slightly present in CCP (spot 2'). Therefore, these spots seemed to be newly appeared in response to hypoxia/reoxygenation. By LC-MS/MS analysis of protein spots 1 and 2, thioredoxin and eukaryote translation initiating factor (eIF) 5A, respectively, were identified.

Example 2

Apoptosis-Inducing Ability of Secreted eIF5A (1) As thioredoxin has been known to act as antioxidant by reducing other proteins and play a protective role against oxidative stress-induced cell injury, eIF5A was considered to be a candidate of an apoptosis inducing humoral factor. eIF5A is the only protein known to contain a unique amino acid hypusine, which is formed post-translationally by two-steps of an enzymatic reaction. eIF5A has been known to be localized mainly in the cytoplasm under normal conditions where hypusinated eIF5A facilitates translation of mRNAs involved in cell proliferation. However, no study to date has reported that eIF5A can be released extracellularly and act as an apoptosis-inducing factor. To confirm that eIF5A is actually released from cardiac myocytes in response to hypoxia/reoxygenation and the released eIF5A can induce apoptosis of cardiac myocytes, quail muscle cells (CRL-1962, ATCC) were transfected with an expression vector containing the FLAG- and His-tagged human eIF5A gene, incubated with hypoxic PBS, and then incubated with normoxic PBS. The reoxygenation-conditioned PBS (RCP) was collected, concentrated, and purified using Ni-NTA Purification System (Invitrogen), and recombinant protein ([RCP] re-eIF5A) was extracted by gel filtration.

(2) Similarly, recombinant human eIF5A ([cytosolic] re-eIF5A) was extracted from cytosolic fractions of the untreated transfected cells.

Figure 2B:
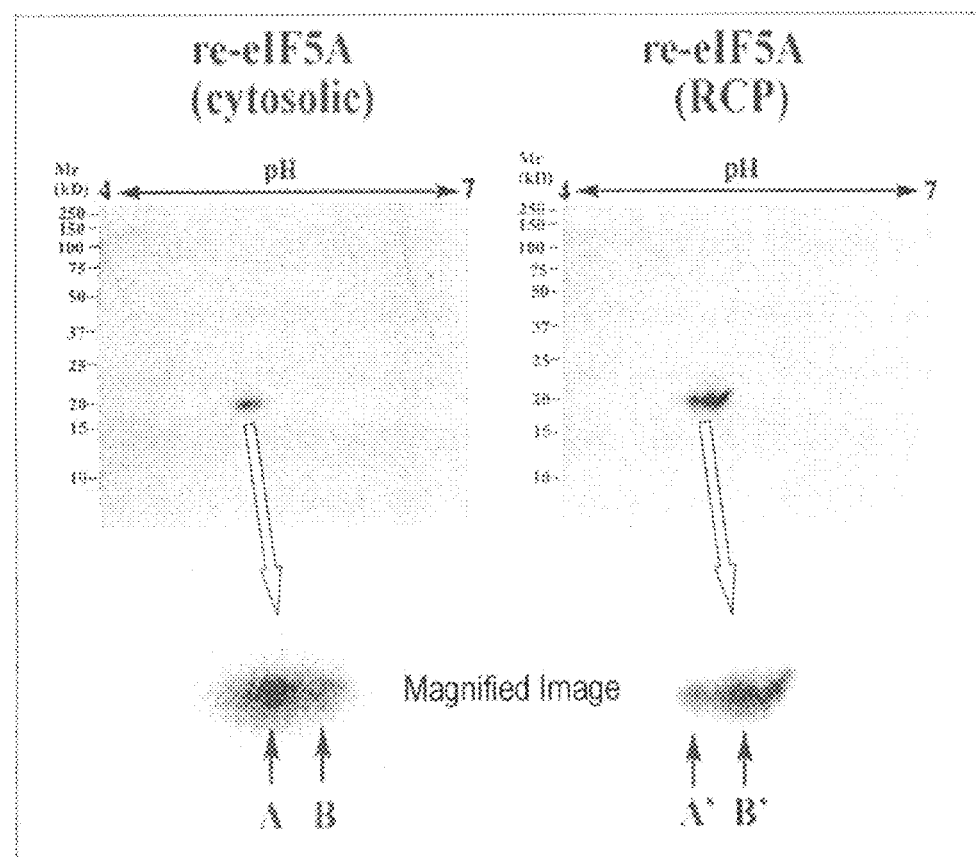
FIG. 2b shows Western analysis of a cytosolic fraction of recombinant eIF5A from untreated transfected cells (cytosolic; left panel) and recombinant eIF5A from RCP (right panel), blotted with anti-FLAG mAb.

(3) After these recombinant eIF5A proteins were separated by two-dimensional electrophoresis, the resultant was analyzed by Western blotting with anti-FLAG M2 mAb (Sigma) (FIG. 2b). The blot with anti-FLAG M2 mAb showed mainly two forms of recombinant eIF5A proteins for both cytosolic and secreted (RCP) eIF5A (FIG. 2b; [A, B] and [A', B']).

Specifically, spots having higher pI values, such as hypusinated eIF5A (spots B and B' in FIG. 2b), and spots having lower pI values, such as unhypusinated eIF5A (spots A and A' in FIG. 2b) were identified. There was no detectable spots of deoxyhypusinated intermediate (references Taylor, C. A., et al. Exp. Cell Res. [2007] 313, 437-449). Recombinant eIF5A derived from RCP (the secreted form in response to hypoxia/reoxygenation) had mainly the hypusinated form (FIG. 2b, right panel; spot B'), while recombinant eIF5A derived from cytosolic fractions of untreated transfected cells had mostly the unhypusinated form (FIG. 2b, left panel; spot A). Here, as the isoelectric points of spots A and B of cytosolic form were 5.3 and 5.4, respectively, and the isoelectric points of spots A' and B' of secreted form were 5.2 and 5.3, respectively, it appeared that the isoelectric point decreased by approx. 0.1 during conversion from an cytosolic protein to a secreted protein. This conversion was further confirmed by two-color Western blotting by using the same gel in (0094) Example 4.

Figure 3A:
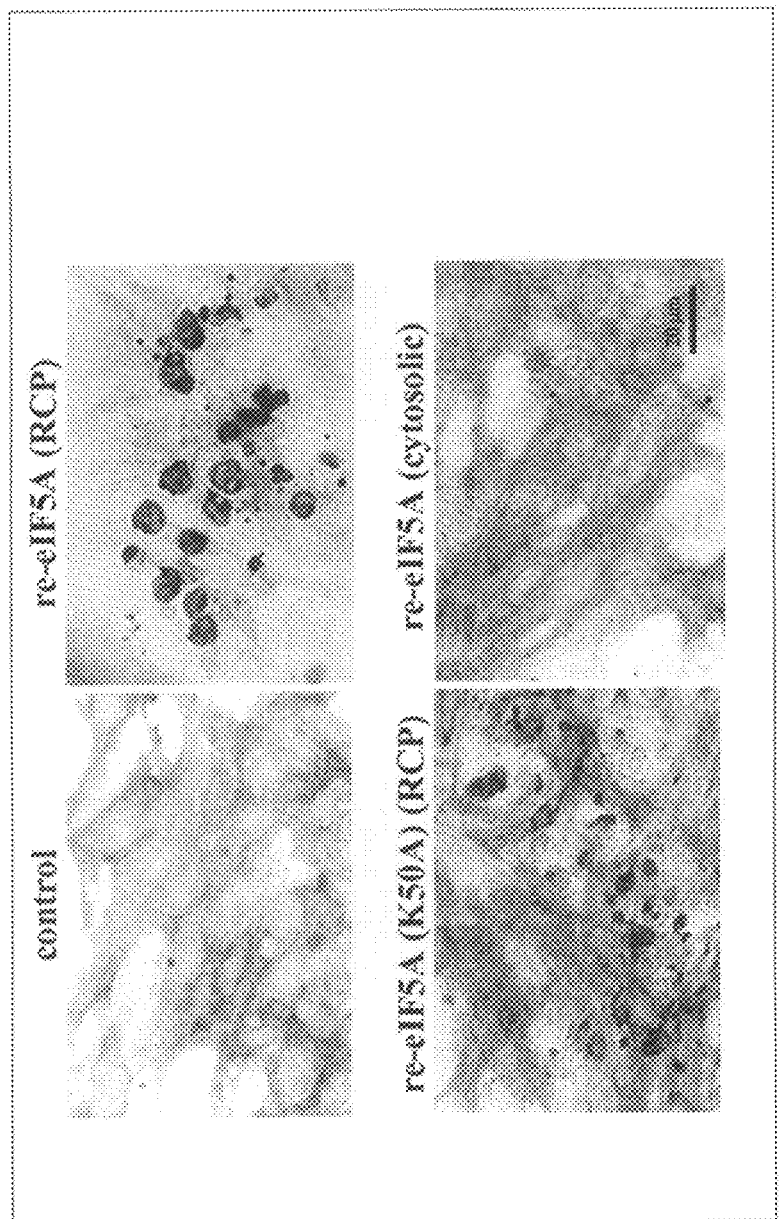
FIG. 3a shows induction of apoptosis of cultured cardiac myocytes due to a recombinant eIF5A protein (10 μg/mL) as determined by double immunostaining for TUNEL (brown color) and cardiac myosin (blue color).
Figure 3B:
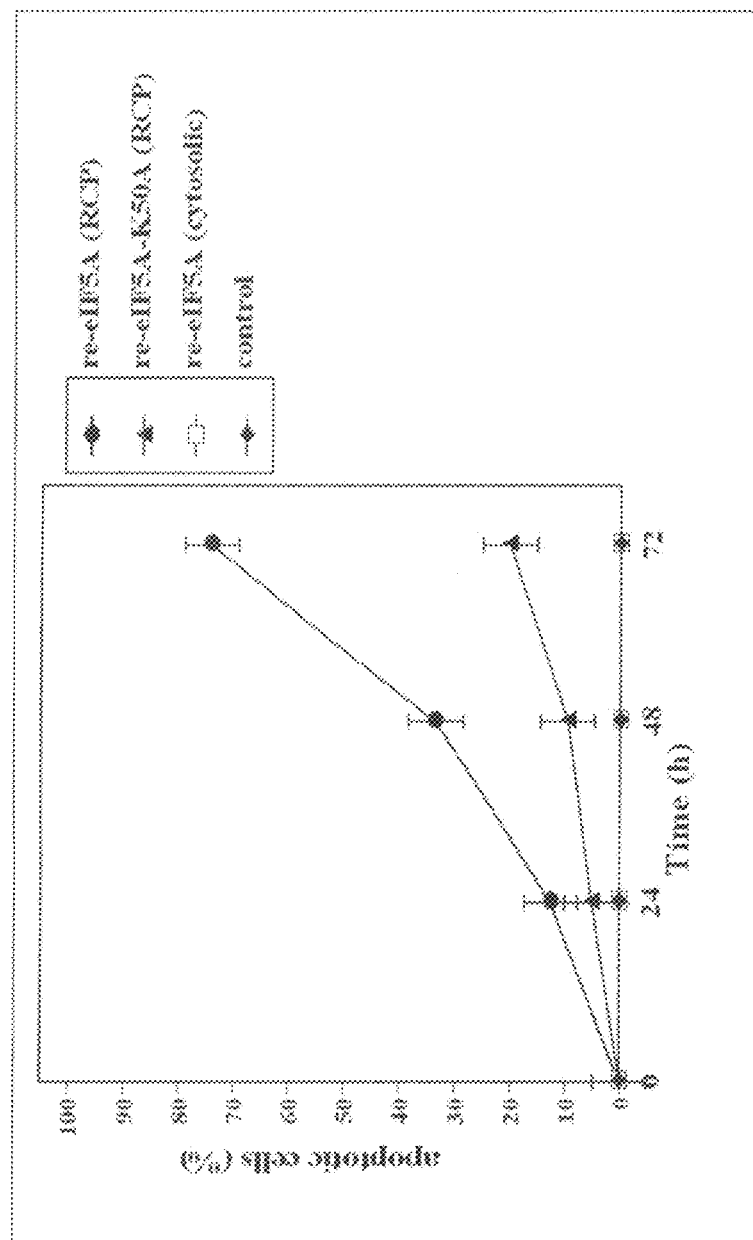
FIG. 3b shows time course of the percentages of apoptotic cardiac myocytes determined by TUNEL staining induced by recombinant eIF5A (RCP), recombinant mutant eIF5A (K50A), and recombinant (cytosolic) eIF5A.
Figure 3C:
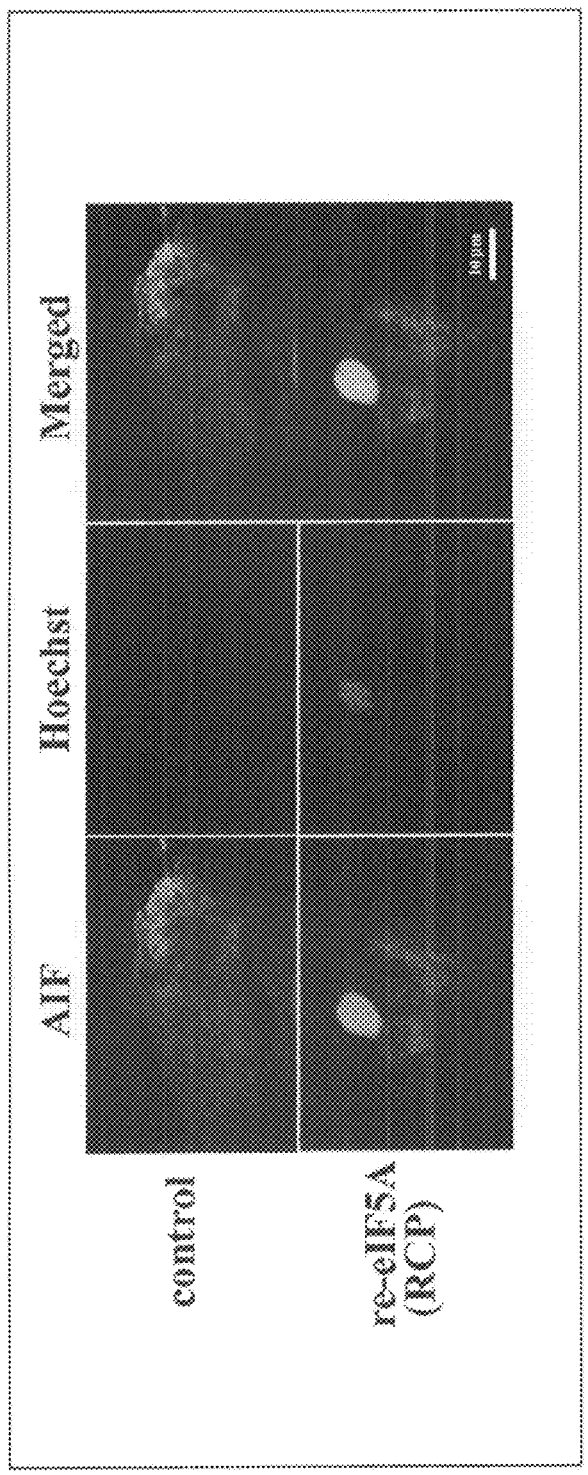
FIG. 3c is a representative confocal image of the effect of recombinant eIF5A (RCP) on subcellular translocation of an apoptosis-inducing factor (AIF) from the cytoplasm to the nucleus.
Figure 3D:
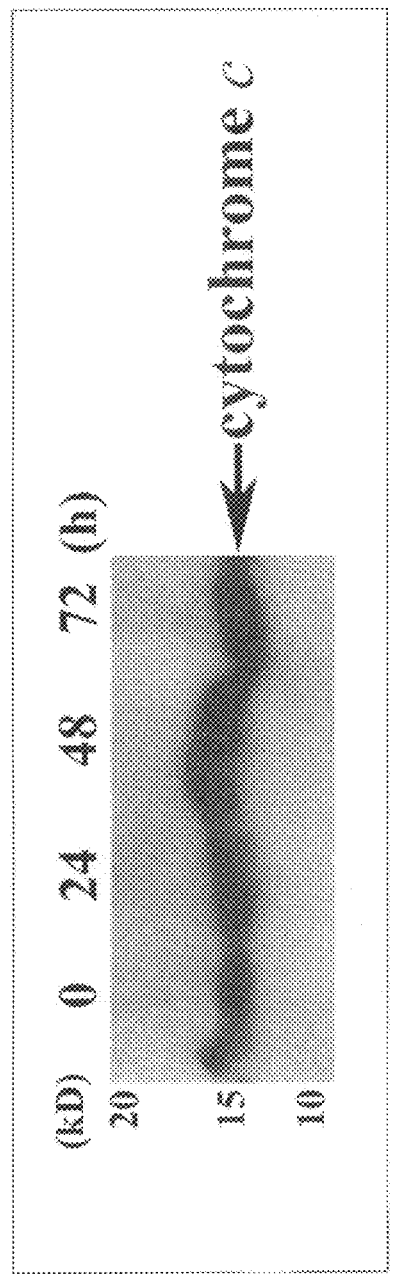
FIG. 3d shows Western blot analysis anti-cytochrome c mAb (7H8.2C12; Lab Vision Corp.) of the effects of recombinant eIF5A (RCP) on cytochrome c released from mitochondria.
Figure 3E:
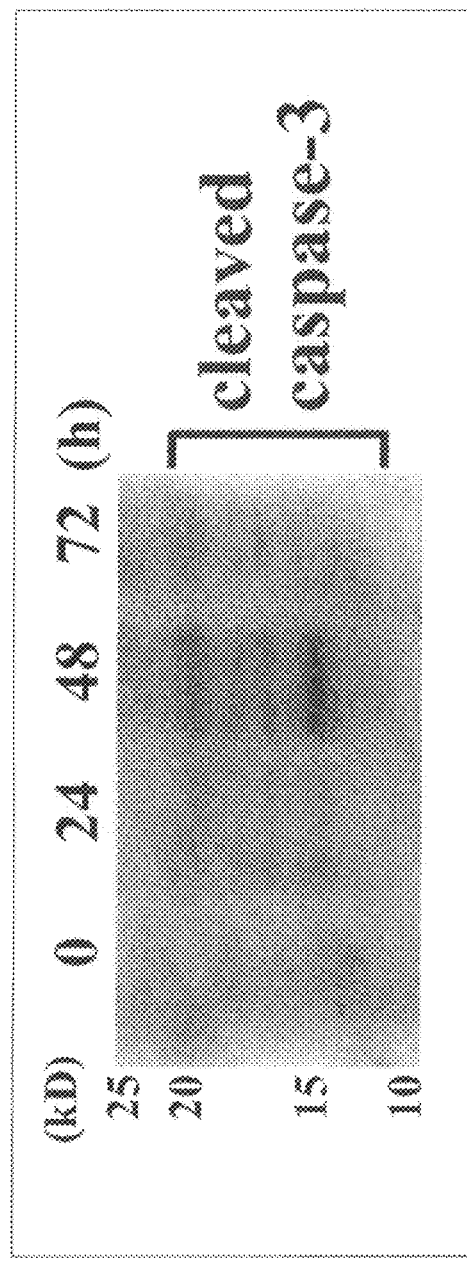
FIG. 3e shows Western blot analysis of the effect of recombinant eIF5A (RCP) on the activation of caspase-3 with anti-caspase-3 polyclonal antibody (H-277; Santa Cruz Biotechnology).
Figure 3F:
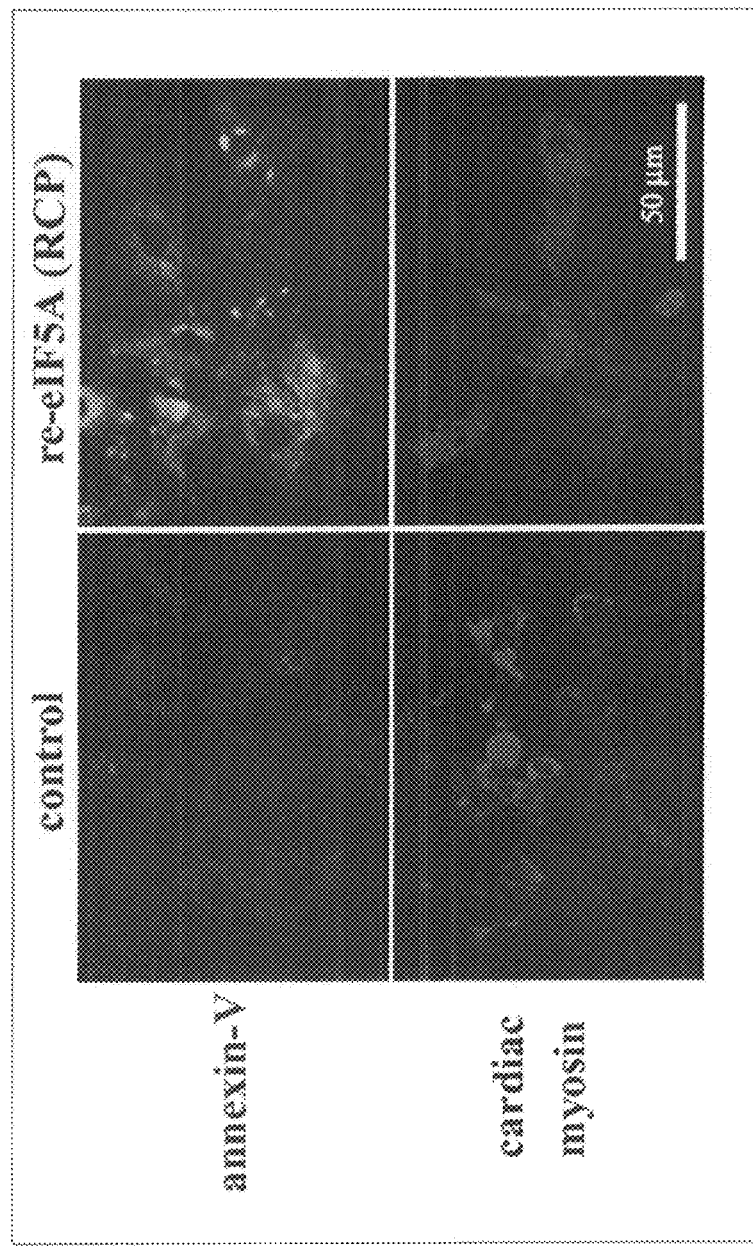
FIG. 3f shows induction of apoptosis of cardiac myocytes as determined by double immunostaining for annexin-V (upper panel, labeled with FITC) and cardiac myosin (lower panel, labeled with TRITC).
Figure 3B:
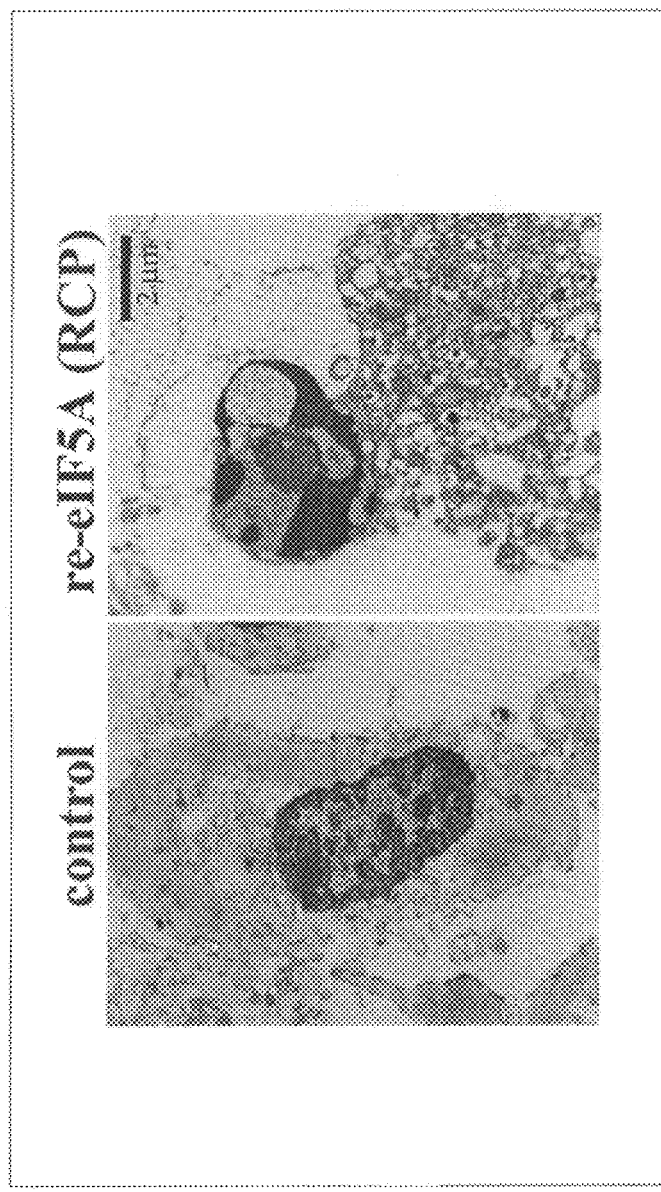
Figure 3A:
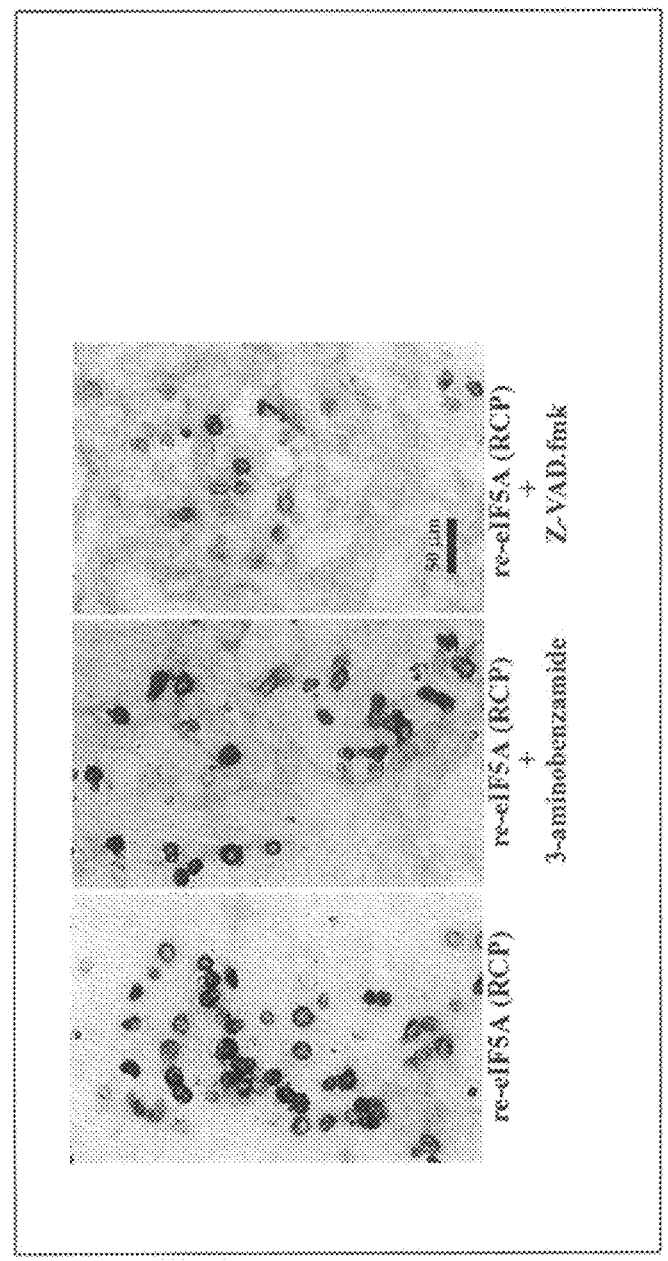

(4) The recombinant eIF5A derived from RCP (mainly containing hypusinated eIF5A) potently induced apoptosis of cultured cardiac myocytes as shown by double staining with terminal deoxynucleotidyl transferase nick-end-label (TUNEL; brown color) and cardiac myosin (blue color) (FIG. 3a), while the recombinant mutant eIF5A (K50A) derived from RCP (unhypusinated eIF5A) only partially induced apoptosis of cardiac myocytes (FIG. 3a). In contrast, in the untreated control group and the cytosolic (mostly unhypusinated) eIF5A-treated group, almost no cardiac myocytes underwent apoptosis (FIG. 3a). FIG. 3b shows time course of percentage of apoptotic cardiac myocytes induced by the recombinant eIF5A (RCP), the recombinant mutant (K50A) eIF5A (RCP), and the recombinant (cytosolic) eIF5A. The recombinant eIF5A(RCP) also induced translocation of the apoptosis-inducing factor (AIF) from the cytosol (mitochondria) to the nucleus in cultured cardiac myocytes as determined by double staining for AIF and Hoechst 33342 (1 $\mu g \cdot mL^{-1}$, FIG. 3c). The recombinant eIF5A (RCP) markedly increased the cytosolic fractions of cytochrome c and the active form of caspase-3 in cultured cardiac myocytes with its peak at 48 hours (FIG. 3d, arrow, and FIG. 3e). The induction of apoptosis of cardiac myocytes by the recombinant eIF5A (RCP) was further confirmed by Annexin-V staining (FIG. 3f) and the hypercondensation of nuclear chromatins by electron microscopy (FIG. 3g).

Example 3

Figure 3I:
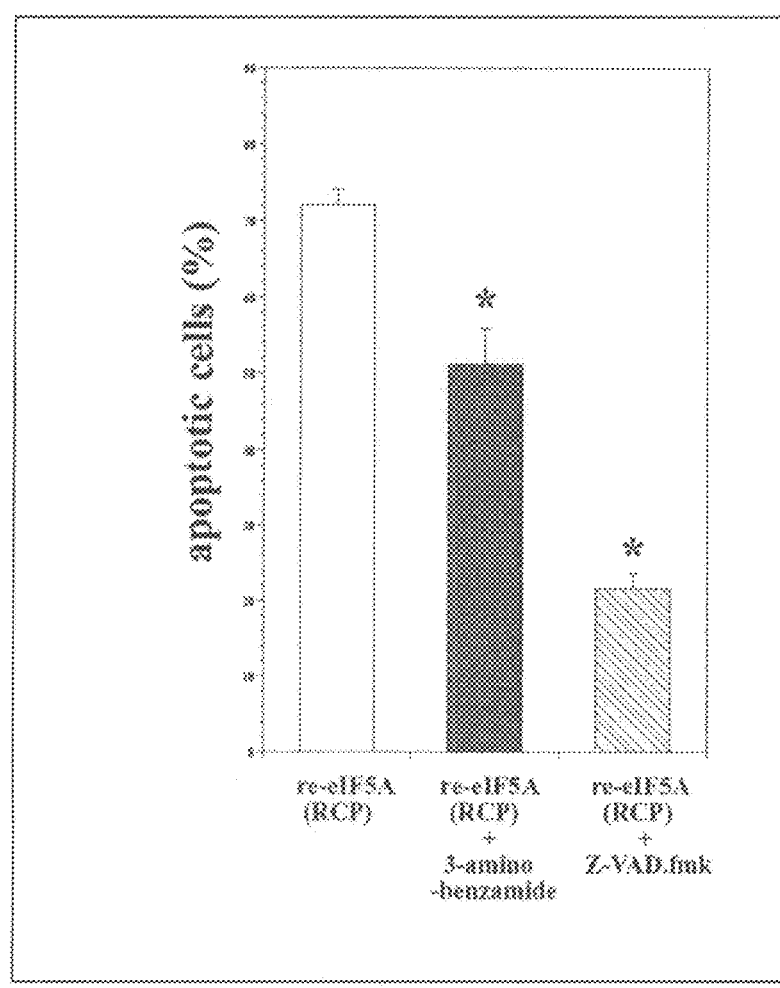
FIG. 3i shows the percentages of apoptotic cardiac myocytes, determined by TUNEL staining at 72 hours after addition of recombinant eIF5A (RCP). Data are expressed as mean±S.D.
Figure 31:
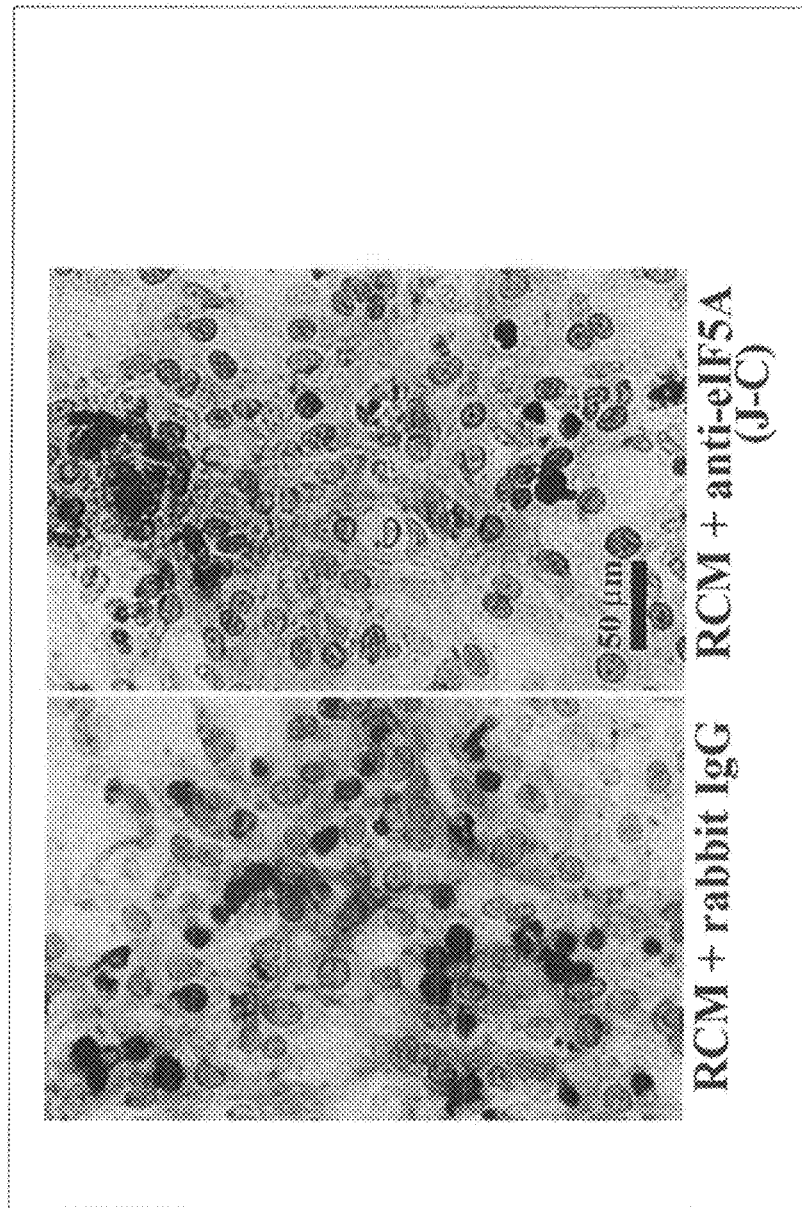
Figure 3K:
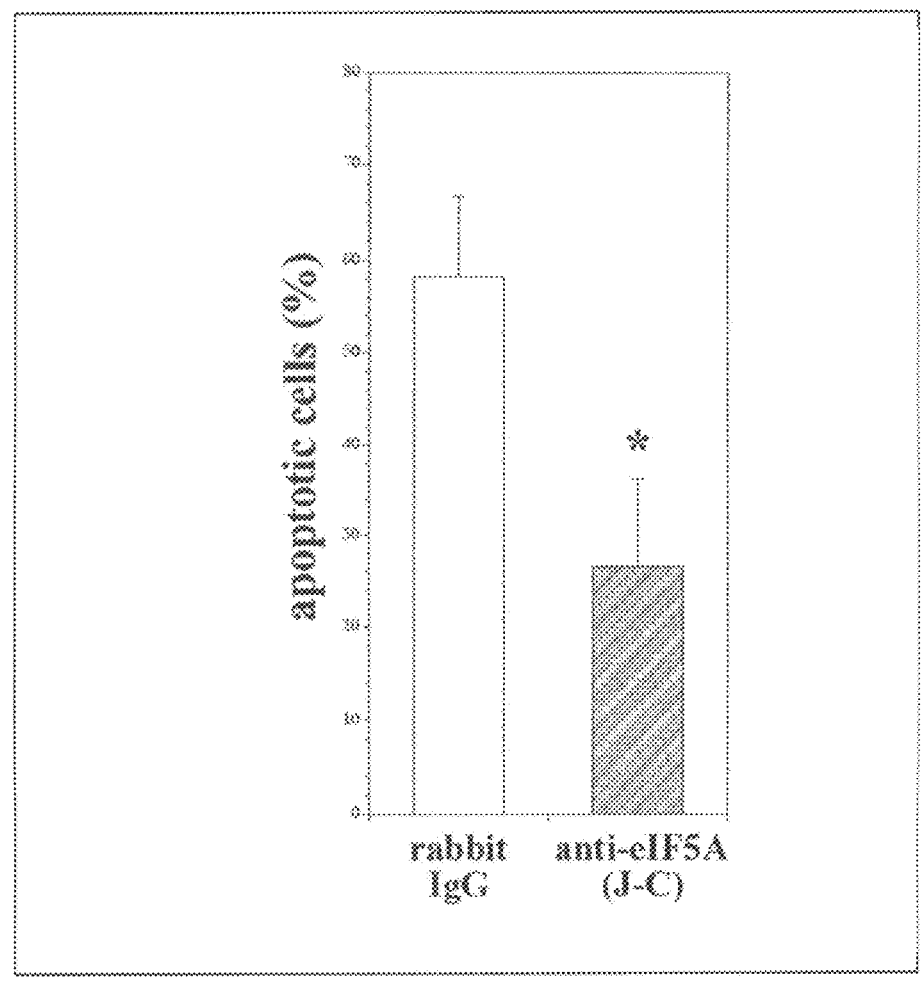
FIG. 3k shows the effect of immunodepletion of eIF5A on reoxygenation-conditioned media (RCM)-induced apoptosis of cardiac myocyte, as percentages of apoptotic cardiac myocytes, which were determined by double immunostaining for TUNEL and cardiac myosin at 30 hours after addition of RCM.

It is known that apoptosis of mammalian cells can be classified into the caspase-dependent pathway and the caspase-independent pathway, and that activation of poly (ADP-ribose) polymerase-1 (PARP-1) signals to mitochondria to release AIF mediates the apoptosis signal cascade in the caspase-independent pathway. Accordingly, to investigate the contribution of the caspase dependent pathway and the caspase independent pathway to the apoptosis of cardiac myocytes induced by recombinant eIF5A (RCP), was analyzed the effects of PARP-1 inhibitor 3-aminobenzamide (Sigma) and broad caspase inhibitor Z-VAD.fmk (BIOMOL International, LP) on induction of apoptosis. FIGS. 3h and 3i show that PARP-1 inhibitor (3-aminobenzamide) and caspase inhibitor (Z-VAD.fmk) significantly inhibited apoptosis induction by approx. 30% and 70%, respectively, which demonstrates the contribution of the both pathways. To confirm that the secreted eIF5A actually mediates hypoxia/reoxygenation-induced apoptosis of cardiac myocytes, the effect of removal of eIF5A from the reoxygenation-conditioned medium (RCM) by using a neutralizing antibody on RCM-induced apoptosis of cardiac myocytes was analyzed. FIGS. 3j and 3k show that removal of RCM-derived eIF5A by using anti-eIF5A antibody (J-C) decreased apoptosis of cardiac myocytes significantly (approx. 55%), which indicates that RCM-induced apoptosis was at least partially mediated by the secreted eIF5A. The reason why immunodepletion of RCM-derived eIF5A did not completely abrogate the induction of apoptosis appears that the neutralizing activity of the antibody was not strong enough to completely deplete eIF5A derived from RCM because the amino acid sequence of eIF5A is highly conserved among mammalians.

Example 4

(Isoelectric Point of Secreted (Hypusinated) eIF5A)

Figure 4:
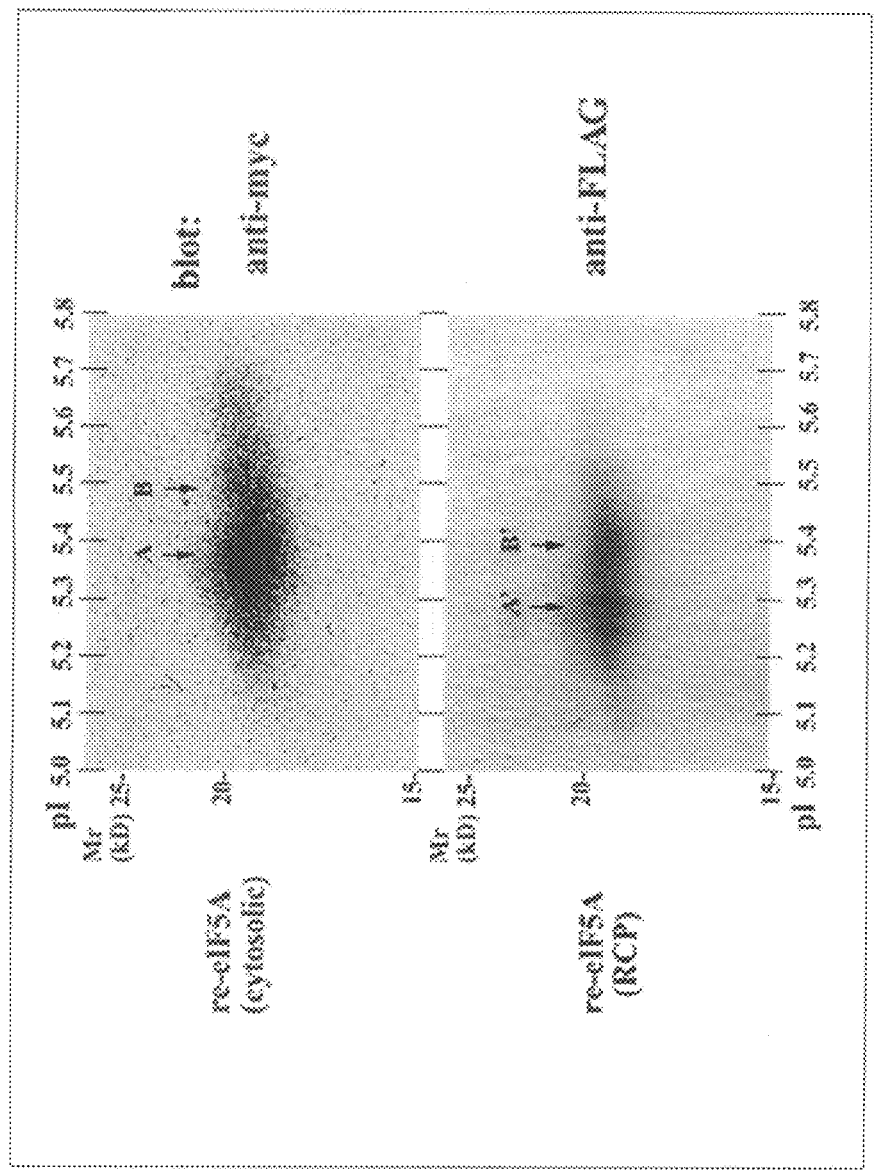
FIG. 4 is a diagram showing two-dimensional electrophoresis results of myc-tagged and FLAG-tagged recombinant eIF5A. The upper panel shows cytosolic eIF5A, and the lower panel shows secreted eIF5A. A is unhypusinated eIF5A, and B is hypusinated eIF5A.

FIG. 4 shows two-dimensional electrophoresis results of the myc- and FLAG-tagged recombinant eIF5A. In the figure, A is unhypusinated eIF5A, and B is hypusinated eIF5A. Specifically, the upper panel of FIG. 4 shows Western blot results of cytosolic fractions of the myc- and His-tagged recombinant eIF5A from transfected cells not treated with RCP. From the upper panel of FIG. 4, it was found that the isoelectric points of the cytosolic eIF5A, that is, conventionally known eIF5A were approx. 5.4 for the cytosolic unhypusinated eIF5A and approx. 5.5 for the cytosolic hypusinated eIF5A. In other words, the isoelectric point of eIF5A is increased by hypusination by 0.1.

Furthermore, the lower panel of FIG. 4 shows Western blot results of the FLAG- and His-tagged recombinant eIF5A from reoxygenation-conditioned PBS (RCP). From the lower panel of FIG. 4, it was found that the isoelectric point of secreted eIF5A decreased by 0.1 as compared with non-secreted (cytosolic) eIF5A. Specifically, the isoelectric point of secreted unhypusinated eIF5 (A') was approx. 5.3, and the isoelectric point of secreted hypusinated eIF5A (B') was approx. 5.4.

Example 5

Figure 5A:
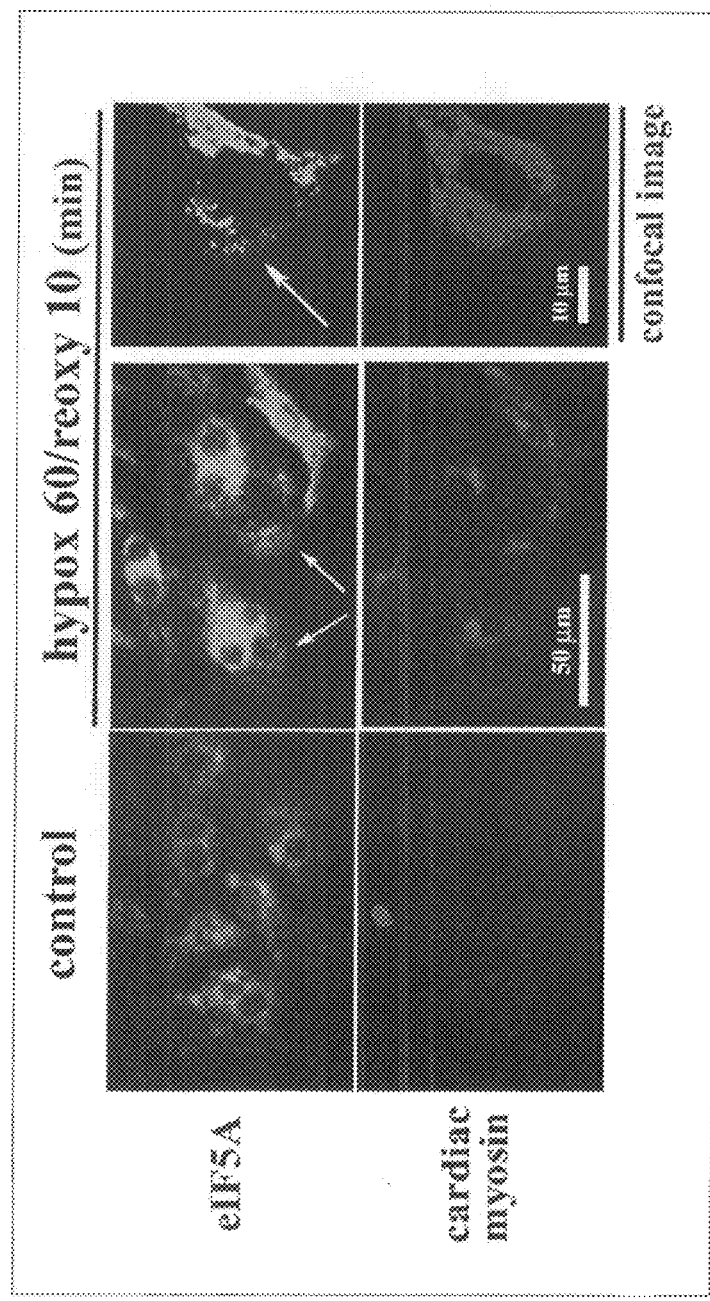
FIG. 5a shows immunofluorescence localization of an eIF5A protein in cultured cardiac myocyte in response to hypoxia/reoxygenation determined by double immunostaining with an anti-eIF5A antibody (J-M) and an anti-cardiac myosin (CMA19).
Figure 5B:
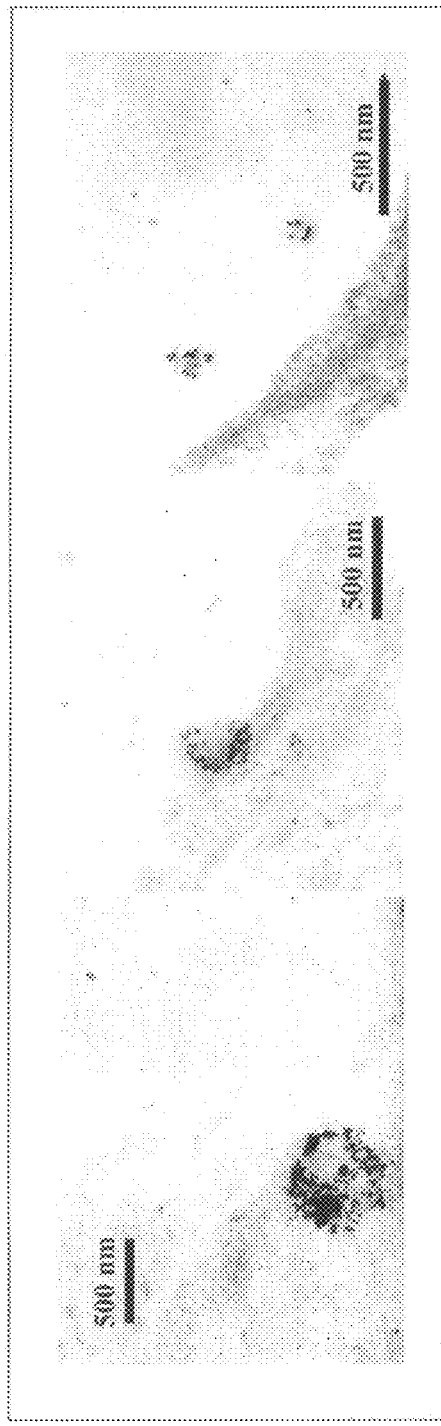
FIG. 5b shows immunoelectron microscopic subcellular localization of an eIF5A protein in cultured cardiac myocyte in response to hypoxia/reoxygenation with an anti-eIF5A antibody (J-M) and Protein A-labeled colloidal gold.
Figure 5C:
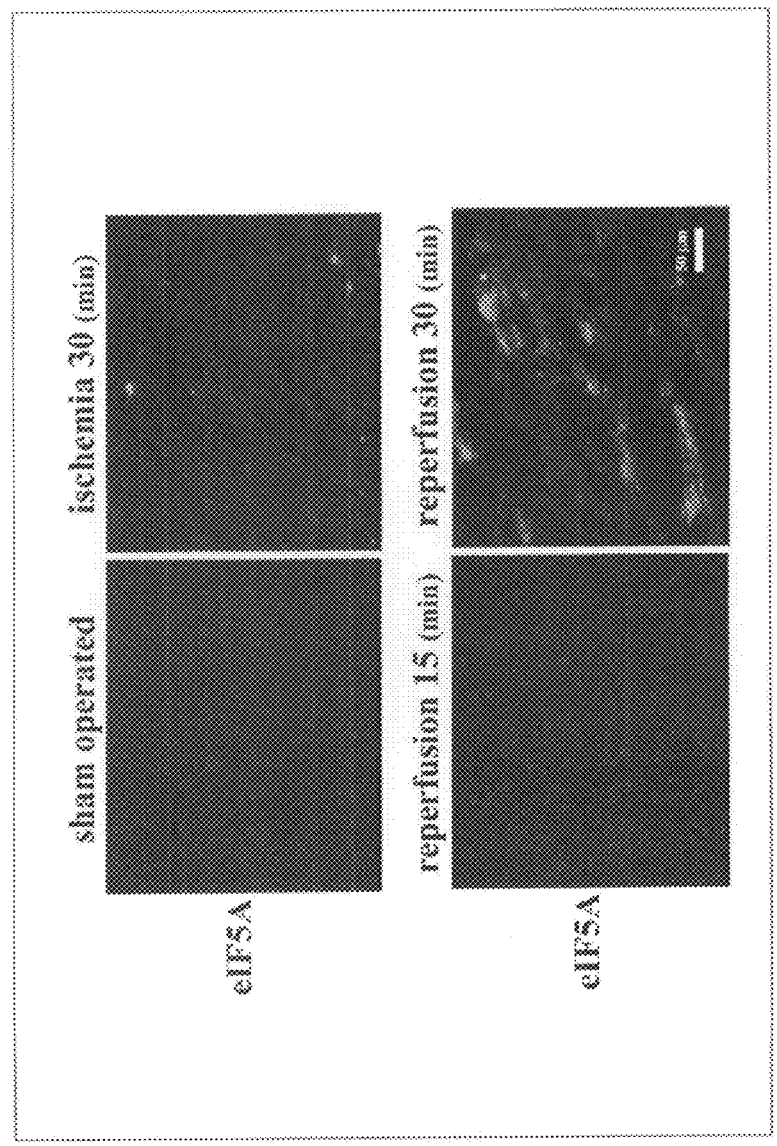
FIG. 5c shows immunofluorescence of an eIF5A protein in myocardial tissues from sham-operated rats and rats subjected to myocardial ischemia/reperfusion in vivo.

Subcellular localization of eIF5A in cultured cardiac myocytes was analyzed by double immunostaining with an anti-eIF5A antibody (J-M) and anti-cardiac myosin (CMA19) antibody. Immunostaining for cardiac myosin showed that most cells were cardiac myocytes (FIG. 5a, lower panel). Cardiac myocytes under normoxia only weakly express eIF5A at the perinuclear region (FIG. 5a, upper left panel). Cardiac myocytes subjected to hypoxia for 60 min and subsequent reoxygenation for 10 min clearly showed granular staining in their peripheral cytoplasm as well as perinuclear region with the anti-eIF5A antibody (J-M) (FIG. 5a, upper middle panel and upper right panel, arrows). Furthermore, immunoelectron microscopy with the anti-eIF5A antibody (J-M) revealed that eIF5A existed in granules immediately adjacent to (FIG. 5b, left panel) or on the plasma membrane (FIG. 5b, middle panel), or away from the plasma membrane as if the granules were being secreted from the cardiac myocytes (FIG. 5b, right panel). This strongly suggests that eIF5A can be secreted from cardiac myocytes in response to hypoxia/reoxygenation like secretary granules. No significant signal was detected in nonimmunized rabbit sera. To confirm the expression of eIF5A on cardiac myocytes in response to in vivo ischemia/reperfusion, eIF5A of ventricular tissues derived from sham-operated rats and derived from rats subjected to myocardial ischemia/reperfusion were immunostained. In the sham-operated rats and the rats subjected to myocardial ischemia for 30 min, eIF5A was hardly expressed on cardiac myocytes (FIG. 5c, upper left and right panels, respectively). Myocardial ischemia for 30 min and subsequent reperfusion for 15 min induced weak expression of eIF5A on the plasma membrane of some cardiac myocytes (FIG. 5c, lower left panel). Myocardial ischemia for 30 min and subsequent reperfusion for 30 min clearly increased the expression of eIF5A on the plasma membrane of many cardiac myocytes (FIG. 5c, lower right panel). This strongly suggests that the same mechanism is involved in cardiac response to ischemia/reperfusion in vivo as to hypoxia/reoxigeneration in vitro.

Example 6

For the intracellular molecular mechanism in cellular response to the oxidative stress, it was reported that the earliest step was activation of Src tyrosine kinases, followed by activation of Ras and Raf-1 in mammalian cells in response to ultraviolet (Cell 71, 1081-1091 [1992]). These intracellular signaling cascades were confirmed in cardiac myocytes in response to in vitro hypoxia/reoxygenation (Circ. Res. 78, 82-90 [1996]; Biochem. Biophys. Res. Commun. 226, 530-535 [1996]). PARP-1 is a nuclear enzyme known to play a role in repair of DNA damage by depleting NAD and ATP, which leads to cell death. Oxygen free radicals cause DNA damage and thereby activate PARP-1. PARP-1 therefore may contribute reperfusion injury of previously ischemic tissue through generation of oxygen free radicals. In fact, inhibition of PARP-1 activity attenuates reperfusion injury of various tissues including myocardium (Proc. Natl. Acad. Sci. 94, 679-683 [1997]).

Example 7

Figure 7:
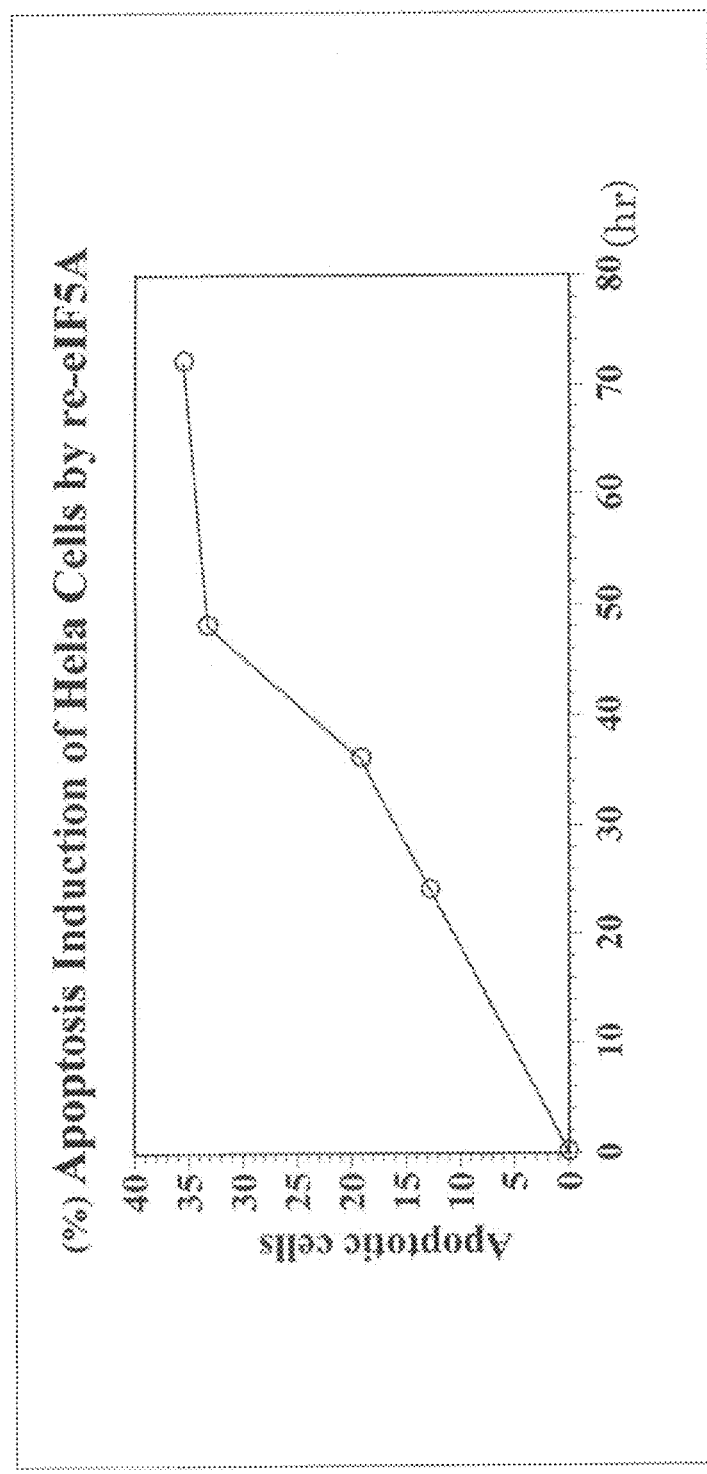
FIG. 7 is a diagram showing changes with time in the apoptosis inducing ability of recombinant eIF5A (re-eIF5A) on Hela cells.

Apoptosis-Inducing Ability of the Secreted eIF5A of the Present Invention in Cancer Cells The results (TUNEL staining) of examination of the apoptosis-inducing ability of the secreted eIF5A of the present invention against various cells are shown in FIGS. 6 and 7. FIG. 6 shows that the recombinant secreted eIF5A of the present invention (10 μg/ml, 30 to 36 hours) induced apoptosis of Hela cells, liver cancer cells, and glioblastoma cells. On the other hand, apoptosis of quail muscle cells, which are normal cells, was not induced until 72 hours.

Example 8

It was found that the recombinant (secreted, mainly hypusinated) eIF5A induced apoptosis of cardiac myocytes through the caspase-dependent pathway and PARP-1-dependent pathway. Production of oxygen free radicals is known to occur within few minutes of reperfusion of the heart (Circ. Res. 61, 757-760 [1987]). Meanwhile, a marked amount of secreted eIF5A was detected in RCP as early as approx. one minute of reoxygenation. It is therefore considered that PARP-1 activation induced by ischemia/reperfusion (or hypoxia/reoxygenation) is mediated independently by production of oxygen free radicals as well as by secretion of hypusinated eIF5A.

In the case of mechanical load, it has been reported that mechanical stretch of cardiac myocytes causes autocrine release of angiotensin II, which then induces activation of multiple intracellular signaling pathways in cardiac myocytes, resulting in cell hypertrophy (Cell. 75, 977-984 [1993]). This indicates that exquisite autocrine mechanism in which cardiac myocytes respond and adapt to the external stress by increasing contractile components against mechanical load through releasing angiotensin II in vivo. In contrast, the present invention revealed that cardiac myocytes respond but fail to adapt to some external stresses, such as strong oxidative stress, by undergoing apoptosis through releasing secreted hypusinated eIF5A. There may be a balance between apoptosis-inducting factors (for example, hypusinated eIF5A and oxygen free radicals) and anti-apoptosis factors (for example, thioredoxin, cyclophilin A, and heat shock protein) in cellular response to the oxidative stress.

When the oxidative stress is strong enough for cardiac myocytes to secrete a sufficient amount of hypusinated eIF5A to cause apoptosis, the balance can be lost. Therefore, neutralization of secreted hypusinated eIF5A or blockade of a cell surface receptor specific for secreted hypusinated eIF5A protects cardiac myocytes from excessive (or lethal) oxidative stress, such as complete ischemia followed by reperfusion. Here, the cell surface receptor of secreted hypusinated eIF5A will be identified.

Although eIF5A is identified as one of eukaryote translation initiation factors (J. Biol. Chem. 251, 5551-5557 [1976]), the function of eIF5A has been only partially understood. As blocking of lysine/hypusine transformation inhibited the translation initiation function and cell proliferation (Mol. Cell. Biol. 11, 3105-3114 [1991]; J. Biol. Chem. 266, 7988-7994 [1991]), the translation initiation activity of eIF5A is known to be correlated with hypusination (unique posttranslational modification) of the specific lysine residue of eIF5A. More recently, it has been reported that unhypusinated eIF5A rapidly traslocates from the cytoplasm to the nucleus and mediates apoptosis in response to TNF (tumor necrosis factor)-α (Exp. Cell. Res. 313, 437-449 [2007]). Overexpression of eIF5A in cancer cells by transfection with eIF5A-expressing adenovirus caused a dramatic accumulation of unhypusinated and deoxyhypusinated eIF5A as compared with hypusinated eIF5A and induced marked apoptosis of the cells. Transfection with (mutant) eIF5A (K50A)-expressing adenovirus caused predominant accumulation of unhypusinated eIF5A and similarly induced marked apoptosis of cells. It was therefore concluded that induction of apoptosis of these cells did not arise from decreases of hypusinated eIF5A, but rather from an accumulation of unhypusinated eIF5A, which seems to induce apoptosis. Accordingly, it was considered that hypusinated eIF5A in cytoplasm contributes to cell proliferation, whereas translocated unhypusinated eIF5A in the nucleus mediates induction of apoptosis.

Therefore, the present invention demonstrated for the first time that hypusinated eIF5A is rapidly secreted from cardiac myocytes in response to hypoxia/reoxygeneration and acts as an apoptosis-inducing ligand by binding to some cell surface receptor on cardiac myocytes. As the secreted unhypusinated eIF5A had significantly decreased the apoptosis-inducing activity than secreted hypusinated eIF5A did, hypusination appears to play a key role in the receptor binding and stimulation. Therefore, the present invention revealed a third mechanism in which eIF5A functions as an apoptosis-inducing ligand in an autocrine fashion in the extracellular space. As eIF5A is not essential for usual protein synthesis, it has been thought that eIF5A may be required for translation of certain mRNAs or, rather be involved in other cellular metabolisms. It is therefore considered that the extracellular function as an apoptosis-inducing ligand, which was revealed by the present invention, is the primary function of this unique protein.

As eIF5A is ubiquitous and abundant among various cell types, it is evident that the autocrine mechanism plays a key role in pathogenesis of oxidative stress-induced cell injury induced by various environment stimuli and that involved in many common diseases caused by an oxidative stress, such as atherosclerosis, aging, and cancer.

Example 9

Figure 9:
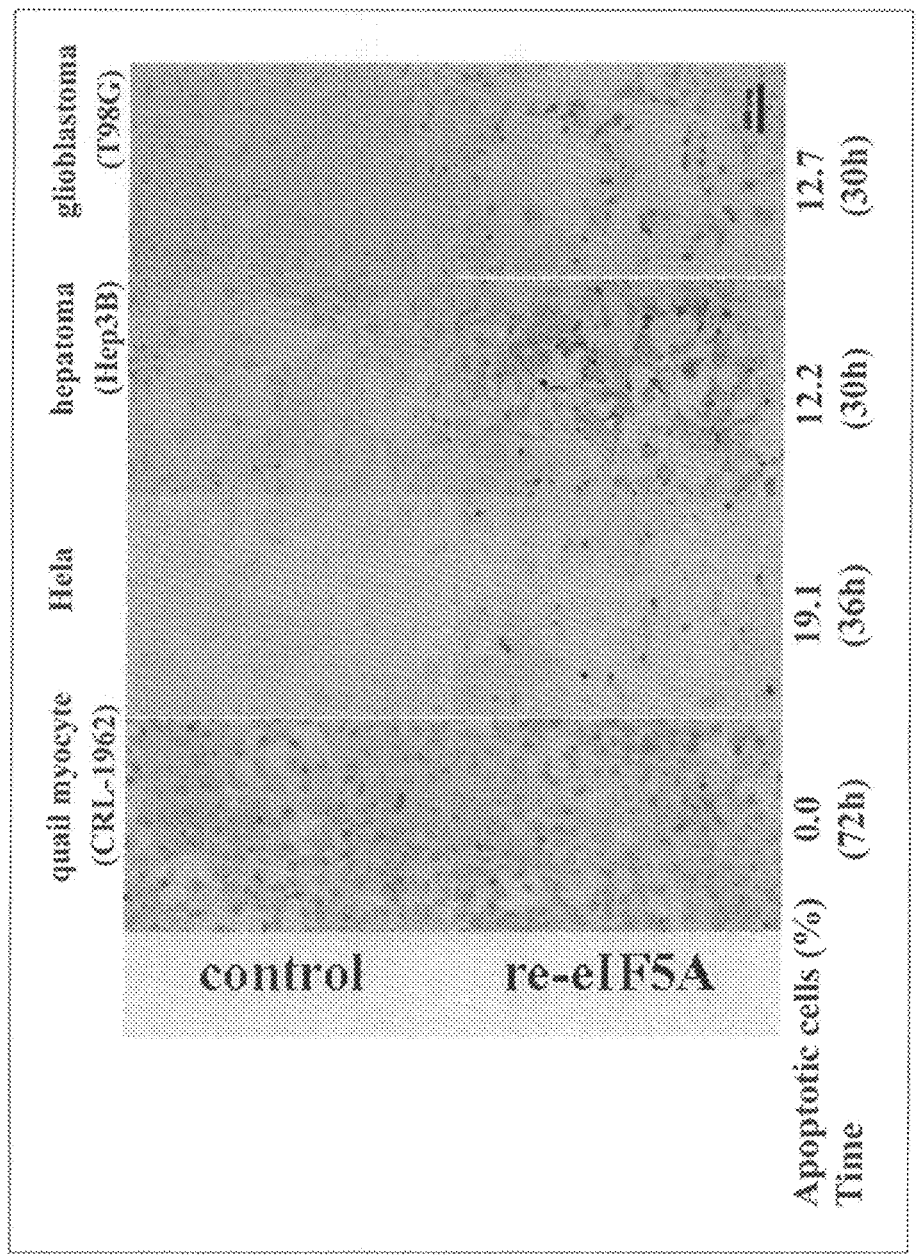
FIG. 9 is a diagram showing the inhibitory effect of an anti-eIF5A neutralizing monoclonal antibody on rat myocardial ischemia/reperfusion injury. The proportion of the infracted area to the whole cross section area of the myocardial tissue is shown on the right side.
Figure 8:
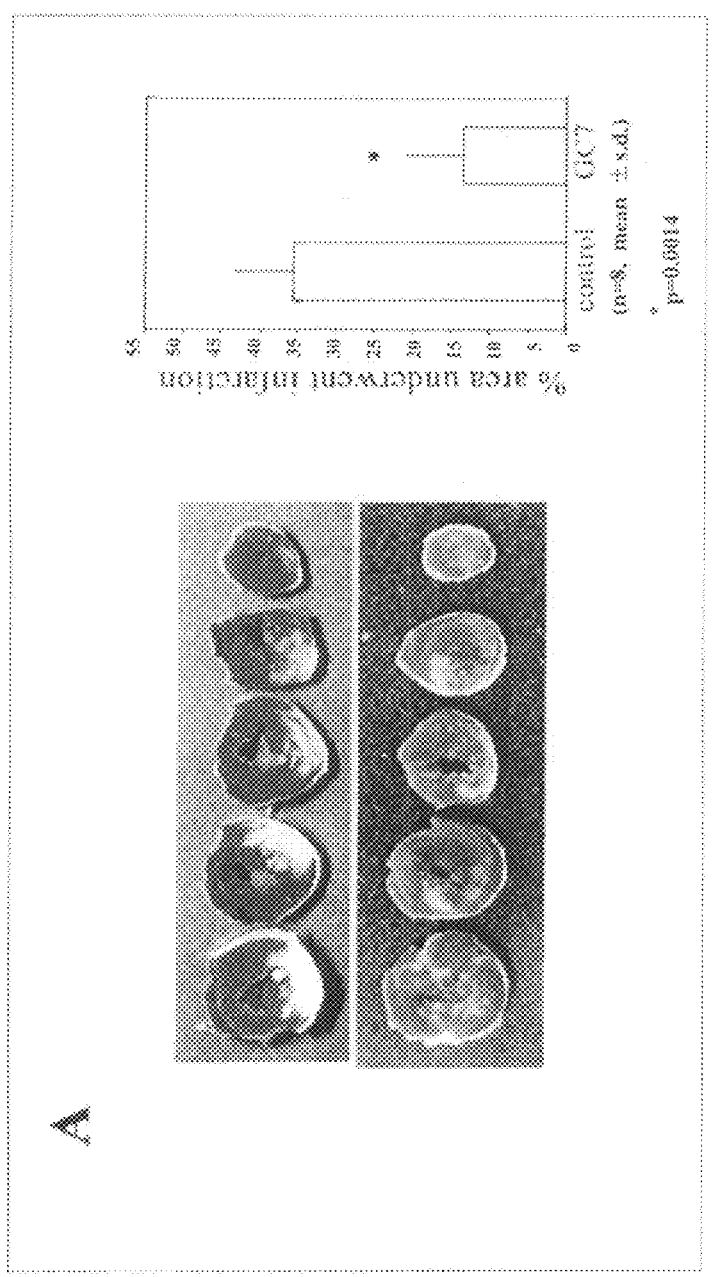
FIG. 8 is a diagram showing the inhibitory effect of a DHS inhibitor (GC7) on rat myocardial ischemia perfusion injury. The proportion of the infracted area to the whole cross section area of the myocardial tissue is shown on the right side.
Figure 9:
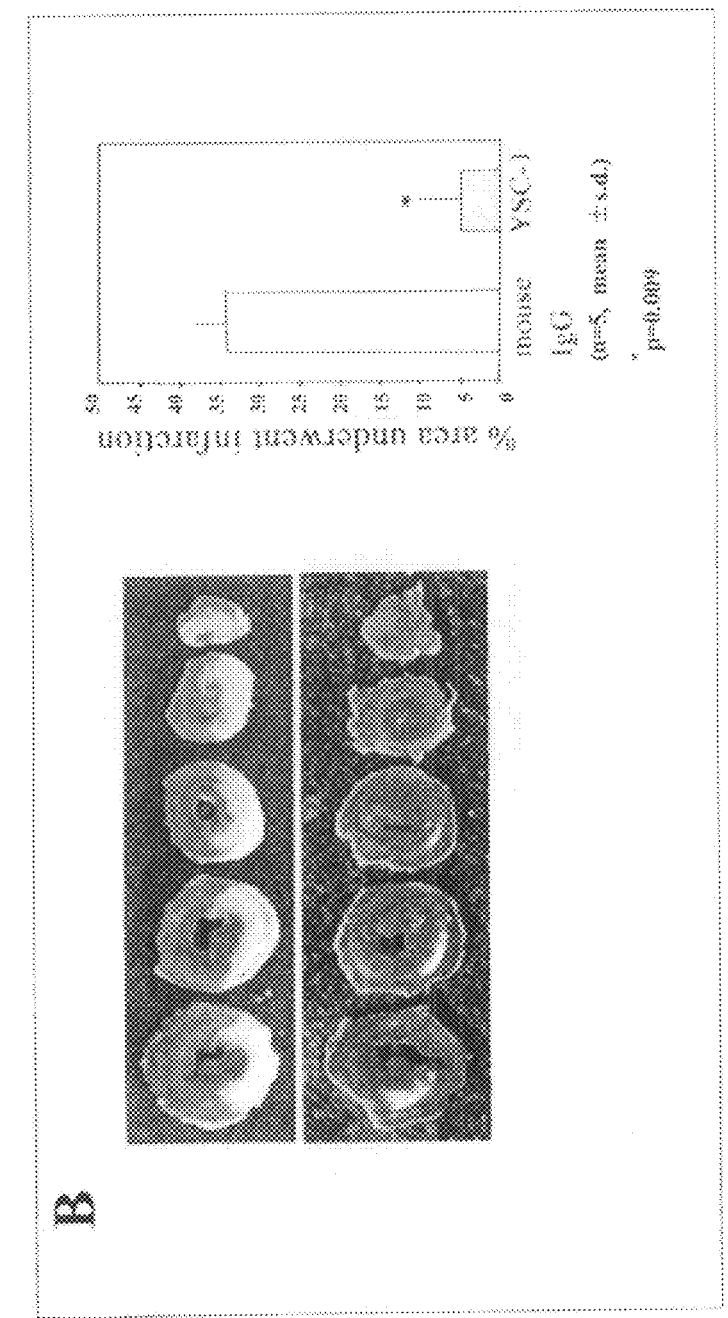

Examination of Effect of Inhibition of Hypusination of eIF5A Using DHS Inhibitor on Rat Myocardial Ischemia/Reperfusion Injury eIF5A is deoxyhypusinated by deoxyhypusine synthase (DHS) in the cytoplasm (deoxyhypusine eIF5A) and then hypusinated by deoxyhypusine hydroxylase (DOHH) (hypusinated eIF5A). eIF5A is further secreted extracellularly by an oxidative stress stimulus as secreted eIF5A and acquire the apoptosis-inducing activity. It is therefore considered that the apoptosis-inducing activity can be reduced by inhibiting hypusination of eIF5A with a DHS inhibitor. Accordingly, (1) the inhibitory effect on myocardial infarction was investigated by administering GC7 (N1-guanyl-1,7-diaminoheptane), a DHS inhibitor, from five days to the day before myocardial ischemia/reperfusion (1 mg/kg, everyday, peritoneal administration). A group similarly to which the solvent of GC7 was administered was established as the control group. In an experimental system for rat myocardial ischemia/reperfusion as mentioned above, complete coronary artery occlusion was performed by clamping the left coronary artery for 30 min, then reperfusion was performed by removing the clamp and the rats were killed 24 hours later. The heart was horizontally sliced from the cardiac apex towards the base of the heart and stained with 1% TTC (trimethyl tetrazolium chloride) solution to determine the extent of myocardial infarction. As shown in FIG. 8, the extent of myocardial infarction for control group was approx. 35.6% (representative example; FIG. 9, upper left panel), whereas that for GC7 administration group was approx. 13.4% (representative example; FIG. 8, lower left panel) and myocardial infarction was significantly inhibited (approx. 1/2.7). This demonstrated that hypusination of eIF5A plays a key role in (myocardial) ischemic reperfusion injury.

Example 10

Examination of Inhibitory Effect on Rat Myocardial Ischemia/Reperfusion Injury Using Anti-eIF5A Neutralizing Monoclonal Antibody (Preparation of Anti-eIF5A Neutralizing Monoclonal Antibody)

Hybridomas were produced by immunizing BALB/c mice with cytosolic recombinant eIF5A, and screened for their inhibitory effects on reoxygenation-conditioned medium (RCM)-induced apoptosis of cardiac myocytes, to thereby obtain a single clone producing an antibody which recognizes cytosolic and secreted eIF5A (designated as YSC-1). The anti-eIF5A neutralizing monoclonal antibody (YSC-1) was administered (3 mg/kg, intravenous injection) at 20 min after the start of myocardial ischemia (10 min before reperfusion), and its inhibitory effect on the development of myocardial infarction was investigated. The group to which mouse IgG was similarly administered was established as the control group. As shown in FIG. 9, administration of the anti-eIF5A neutralizing monoclonal antibody (YSC-1) markedly (approx. 7/8) reduced the extent of myocardial infarction to approx. 4.2% (representative example; FIG. 9, lower left panel) as compared with the control group (approx. 34.3%) (representative example; FIG. 9, upper left panel). The above findings suggested that secreted eIF5A conclusively mediates ischemia/reperfusion injury and that the anti-eIF5A neutralizing monoclonal antibody therapy is very useful for prevention of the ischemia/reperfusion injury.

Example 11

Figure 10:
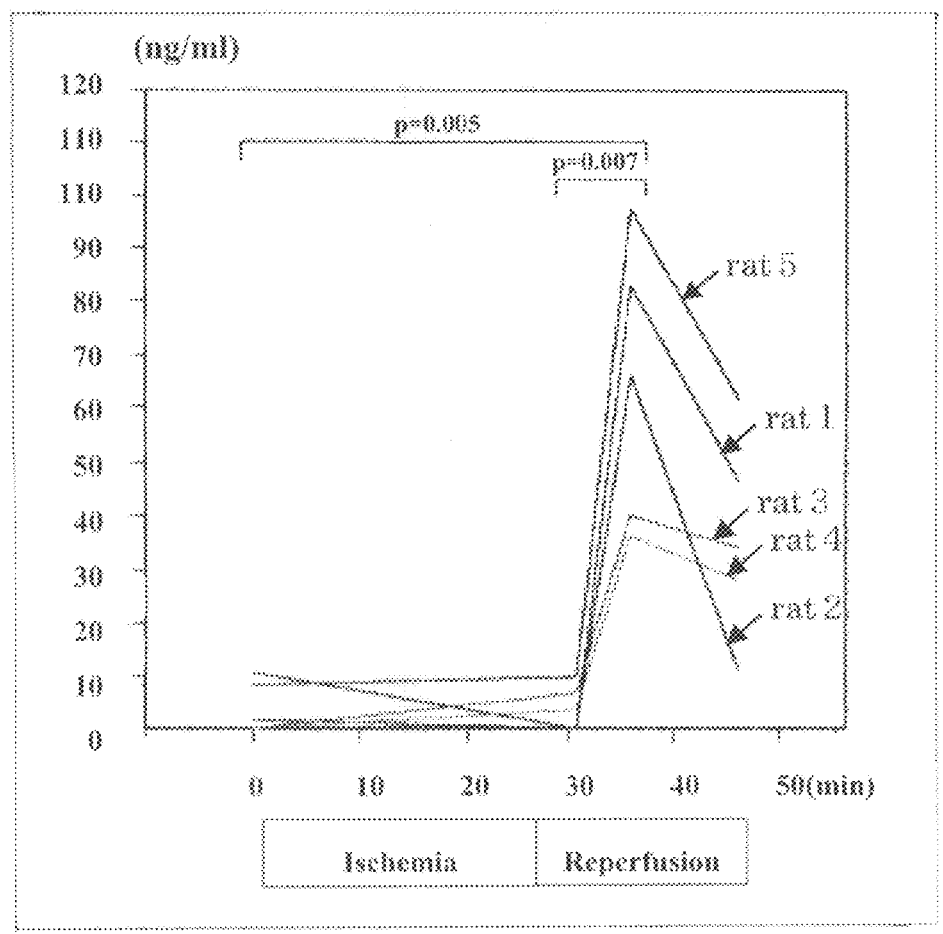
FIG. 10 is a diagram showing serum level of secreted eIF5A in myocardial ischemic reperfusion injury. The p value was calculated by paired t-test (n=5).

To investigate the action of secreted eIF5A in myocardial ischemia/reperfusion injury, a direct ELISA system was developed using a biotinylated anti-eIF5A antibody (J-M) as detecting antibody and streptavidin horseradish peroxidase (HRP), and serum secreted eIF5A levels in rats subjected to myocardial ischemia/reperfusion were examined. No significant change was observed in serum secreted eIF5A levels between the control condition (before ischemia) and at 30 min after ischemia (before reperfusion). The serum secreted eIF5A levels significantly increased at 5 min after reperfusion (64.47±11.18 ng/ml), as compared with that before ischemia (4.04±2.22 ng/mL [mean±SE]: p=0.005) and that at 30 min after ischemia (4.00±1.90 ng/mL: p=0.007). The serum secreted eIF5A levels gradually decreased at 15 min after reperfusion (FIG. 10).

The invention claimed is:

1. A method for inhibiting apoptosis in cardiac myocytes, comprising administering a secreted eIF5A protein inhibitor, wherein an isolated secreted e1F5A protein has an isoelectric point of 5.4 to 5.3 and 0.1 lower than the isoelectric point of a cytosolic e1F5A protein;
the isolated secreted e1F5A protein and the cytosolic e1F5A protein comprise the amino acid sequence of SEQ ID NO:4 and
the secreted e1F5A protein inhibitor is an anti-e1F5A monoclonal antibody.

2. A method of treating myocardial ischemia/reperfusion injury in a subject in need thereof, comprising administering to the subject an effective amount of a secreted eIF5A protein inhibitor or of a pharmaceutical composition comprising a secreted eIF5a protein inhibitor and a pharmaceutically acceptable carrier,
wherein an isolated secreted e1F5A protein has an isoelectric point of 5.4 to 5.3 and 0.1 lower than the isoelectric point of a cytosolic e1F5A protein;
the isolated secreted e1F5A protein and the cytosolic e1F5A protein comprise the amino acid sequence of SEQ ID NO:4 and
the secreted e1F5A protein inhibitor is an anti-e1F5A monoclonal antibody.

* * * * *